_US005863502A_

United States Patent [19]
Southgate et al.

[11] Patent Number: 5,863,502
[45] Date of Patent: Jan. 26, 1999

[54] PARALLEL REACTION CASSETTE AND ASSOCIATED DEVICES

[75] Inventors: Peter David Southgate, Monmouth Junction; Zygmunt Marian Andrevski, Princeton; William Ronald Roach, Rocky Hill; Peter John Zanzucchi, Lawrenceville, all of N.J.

[73] Assignee: Sarnoff Corporation, Princeton, N.J.

[21] Appl. No.: 786,956

[22] Filed: Jan. 23, 1997

Related U.S. Application Data

[60] Provisional application No. 60/010,513, Jan. 24, 1996.

[51] Int. Cl.⁶ .................................................. G01N 21/03
[52] U.S. Cl. .......................... 422/58; 422/61; 422/102; 436/165; 436/180
[58] Field of Search ................................. 422/50, 58, 60, 422/61, 62, 68.1, 82.05, 100, 102, 104; 436/63, 165, 180

[56] References Cited

U.S. PATENT DOCUMENTS

| | | | |
|---|---|---|---|
| 3,690,836 | 9/1972 | Buissiere et al. | 436/165 X |
| 4,761,381 | 8/1988 | Blatt et al. | 436/165 |
| 4,849,340 | 7/1989 | Oberhardt | 435/13 |
| 5,154,888 | 10/1992 | Zander et al. | 422/58 |
| 5,208,163 | 5/1993 | Charlton et al. | 436/63 |
| 5,215,713 | 6/1993 | Steinbiss | 422/61 |
| 5,288,463 | 2/1994 | Chemelli | 422/58 |
| 5,372,946 | 12/1994 | Cusak et al. | 436/69 |
| 5,587,128 | 12/1996 | Wilding et al. | 422/50 |
| 5,605,662 | 2/1997 | Heller et al. | 422/68.1 |
| 5,627,041 | 5/1997 | Shartle | 435/7.24 |
| 5,631,166 | 5/1997 | Jewell | 436/45 |
| 5,652,149 | 7/1997 | Mileaf et al. | 436/518 |

OTHER PUBLICATIONS

Copy of International Search Report dated May 22, 1997, from corresponding international application PCT/US97/00298.

*Primary Examiner*—Harold Y. Pyon
*Attorney, Agent, or Firm*—William J. Burke

[57] ABSTRACT

The invention provides a parallel reaction device for conducting reactions therein comprising one or more reaction flow-ways, each such reaction flow-way comprising one or more chambers connected serially by fluid exchange channels, additional fluid exchange channels connecting such reaction channels in parallel, valve means for initiating and impeding the flow of fluids through such fluid exchange channels, and means for moving the flow of fluids into and out of such chambers.

21 Claims, 16 Drawing Sheets

PARALLEL REACTION CASSETTE AND ASSOCIATED DEVICES

This invention was made with U.S. Government support under Contract No. 70NANB5H1037. The U.S. Government has certain rights in this invention.

CROSS-REFERENCES TO RELATED APPLICATIONS

This non-provisional U.S. national application, filed under 35 U.S.C. 111 (a) claims, under 35 U.S.C. 119(e)(1), the benefit of the filing date of provisional U.S. application Ser. No. 60/010,513, filed under 35 U.S.C. 111 (b) on Jan. 24, 1996.

The present invention relates to a disposable parallel reaction device for conducting reactions, which device can include a component containing all necessary supply and reaction chambers and connecting fluid exchange channels. The parallel reaction device is particularly adapted for conducting polymerase chain reaction ("PCR") assays, and other scientific, forensic and diagnostic assays. Synthetic reactions, including combinatorial chemistry, can also be conducted in the device.

The PCR assay has provided a powerful method of assaying for the presence of either defined segments of nucleic acids or nucleic acid segments that are highly homologous to such defined segments. The method can be used to assay body fluids for the presence of nucleic acid specific for particular pathogens, such as the mycobacterium causing Lyme disease, the HIV virus or other pathogenic microbes. The microbe diagnostic assay functions by adding, to a sample that may contain a target segment of nucleic acid from the microbe's genome, at least one pair of "primers" (i.e., relatively short nucleic acid segments or nucleic acid analogs) that specifically bind to (i.e., "hybridize" with) the target segment of nucleic acid. The first primer of a pair binds to a first strand of the two-stranded target nucleic acid segment and, when hybridized, can prime the enzymatic reproduction of a copy of the second strand of the target nucleic acid segment in a direction arbitrarily designated as the downstream direction. The second primer of a pair binds to the second strand of the target nucleic acid segment at a position downstream from the first primer hybridization site and can prime the enzymatic reproduction of a copy of the first strand of the target nucleic acid segment in the upstream direction. (In the case where the sample is made up of single-stranded target nucleic acids, the second primer will hybridize with the theoretical second strand determined with the Watson-Crick base-pairing rules.) To the sample are added the monomer building blocks of nucleic acid and an enzyme that specifically catalyzes nucleic acid reproduction from a single strand of nucleic acid to which the short primer is bound. The enzyme is preferably highly resistant to destruction by elevated temperatures. The sample is heated to a DNA melting temperature to separate the two strands of the sample nucleic acid and then cooled to a replication temperature. The replication temperature allows the primers to specifically bind to the separated strands and allows the reproductive enzyme to operate. After this cycle, the reaction mix contains two sets of the two stranded nucleic acid segment for each target nucleic acid segment that was originally present. Heating and replication temperature cycles are repeated until sufficient amounts of the nucleic acid segment are created through this exponential reproduction method. For instance, after 20 cycles the segment has been amplified as much as $2^{20}$-fold, or roughly 1,000,000-fold.

There are at least four critical problems associated with automating the PCR reaction. First, the degree of amplification achieved by the assay creates a large risk of contamination from foreign DNA from handling. Thus far, this risk has been dealt with in commercial, manual procedures by conducting the reactions in "clean" facilities that are extremely expensive to construct and maintain. For automation, this risk implies that all the reagents needed and the reaction chamber for the amplification should be contained in a disposable platform in which the sample can be inserted in a controlled, one-time operation. This risk also implies that sample preparation steps should be minimized and, to the extent possible, conducted within a disposable platform.

Second, the high temperatures needed to "melt" the nucleic acid so that the two strands separate imply that the reaction chamber must be well-sealed against vapor loss, even while allowing the insertion and removal of various reagent fluids. This goal is particularly hard to achieve on a suitable, disposable platform.

Third, the reactions should be conducted in relatively small volumes, generally volumes of no more than about 100 µl, to conserve expensive reagents and minimize the amount of sample, which could be a precious sample fluid or tissue that must be conserved to allow for other types of testing or is available only in a small amount.

Fourth, to provide assurance that a positive or negative result is meaningful, it is preferable to perform multiple, parallel reactions (for example, on positive and negative controls, in addition to the sample) using the same reagents for each reaction.

Recently, there have been a number of publications on the mechanics of operating micro-scale reactors. These reactors are often described as constructed on silicon-based materials using the etching techniques developed by the semiconductor industry. This literature, however, does not present an effective solution to the problem of how to operate a disposable, high temperature microreactor. The present invention provides an economical, high temperature microreactor with effective valves suitable for use in conducting multiple, parallel PCR assays, each using the same reagents to assure meaningful results. The microreactor is also suitably adapted for conducting automated assays even when high temperature and considerably high vapor pressure are not a particular concern.

SUMMARY OF THE INVENTION

In one embodiment, the present invention provides a device for conducting parallel reactions, comprising:
  (a) a cassette formed of a body having an upper surface, a lower surface, and an edge, and including an upper film or a lower film attached to the upper or lower surface, respectively, wherein the upper or lower film is formed of a flexible material;
  (b) two or more reaction flow-ways in the cassette, wherein each reaction flow-way comprises two or more fluid chambers which comprise a first supply chamber and a first reaction chamber having an upper wall and a lower wall, and wherein the fluid chambers are serially connected by first fluid exchange channels;
  (c) a valve for controlling the flow of fluid through a first fluid exchange channel;
  (d) a pump for moving fluids into or out of the fluid chambers; and
  (e) a first inlet port on the cassette connected to a first supply chamber in each reaction flow-way by a second fluid exchange channel.

The first supply chamber is preferably a supply chamber having a releasable seal blocking the outlet into the first fluid exchange channel connecting the first supply chamber to its reaction flow-ways; more preferably, the first supply chamber is an internal-outlet supply chamber. The pump preferably comprises a foot-pad pump with foot-pads designed to push on the first supply chamber to open the sealed outlet and pump fluid into the connected first fluid exchange channel. Preferably, the first supply chamber is collapsible upon evacuation and fillable from a vacuum-collapsed state to a defined volume.

In one aspect of the invention, the second fluid exchange channel is releasably sealed so as to block the flow of fluids through the second fluid exchange channel. Preferably, the second fluid exchange channel is heat-sealed; more preferable, the second fluid exchange channel is sealed at multiple locations to prevent fluid communication between the first supply chambers.

In another aspect, the valve used in the context of the present invention is a plunger-type valve that is controlled by a pressure control means for:

(i) applying a positive pressure to the plunger-type valve such that the plunger-type valve presses against the upper or lower film so as to impede the flow of fluid in a first fluid exchange channel, and (ii) releasing the positive pressure to the plunger-type valve such that the plunger-type valve releases from the flexible film so as to permit the flow of fluid in the first fluid exchange channel. Preferably, the plunger of the plunger-type valve is affixed to an instrument from which the cassette is detachable.

The cassette can be formed of a body that comprises recesses in its upper or lower surface which, together with an associated upper or lower film, form the first and second fluid exchange channels, and a plurality of fluid chambers. In the invention, it is preferred that a fluid chamber is formed in the upper or lower surface and at least one first or second fluid exchange channel is formed on an upper or lower surface located above or below that fluid chamber. The cassette of the present invention further comprises:

(f) at least one hole situated in the body so as to connect a first or second fluid exchange channel formed at the upper or lower surface of the body with a first or second fluid exchange channel formed at the other surface.

Preferably, the portion of upper or lower film covering a said fluid chamber made up of a recess in the body is embossed to mirror the shape of the bottom of the fluid chamber such that when the chambers is evacuated the film portion will invert to match the shape of the bottom of the chamber. Preferably, one of the pumps is a foot-pad pump having a foot pad that fits against the surface of the inverted embossed film portion of said fluid chamber.

Preferably, the cassette further comprises:

(g) one or more second supply chambers, wherein two or more fourth fluid exchange channels connect the second supply chamber to two or more reaction flow-ways, which fourth fluid exchange channels include two or more said valves so that fluid from the second supply chamber can be directed to any one of the connected reaction flow-ways to the exclusion of the other connected reaction flow-ways; and (h) one or more second inlet ports on the cassette each connected to one of the second supply chambers by a separate third fluid exchange channel.

Preferably, the device further comprises (i) a metering chamber interposed between the second supply chamber and the connected reaction flow-way.

The combination of elements (f), (g), (h), and optionally (i) forms a sample insertion device. Preferably, the cassette has more than one such sample insertion device and sufficient reaction flow-ways such that different experimental samples can be reacted in parallel.

Preferably, the upper and lower walls of each first reaction chamber are formed of an embossed portion of a said upper film and an embossed portion of a said lower film, wherein the embossing allows upper and lower walls of the first reaction chambers to be brought together to minimize the volume of the first reaction chambers. Preferably, at least one pump comprises a foot-pad pump with upper and lower foot-pads designed to push together the upper and lower walls of a first reaction chamber. Alternatively or in addition, at least one of the pumps comprises gas pressure conduits for applying a positive pressure to the flexible upper or lower walls of a first reaction chamber so as to cause the flexible upper or lower wall to press inward thereby decreasing the volume within the first reaction chamber and impelling the flow of fluids therefrom.

In a preferred embodiment, the cassette further comprises (j) one or more waste chambers; and (k) an exhaust port for evacuating one or more of the first reaction chambers or the waste chambers.

Each embodiment of the invention can further comprise (l) a heater for heating one or more of the fluid chambers;

(m) a cooler for cooling one or more of the fluid chambers; and (n) a temperature monitor for monitoring the temperature of one or more of the fluid chambers. Preferably, a foot-pad for pumping fluid out of the fluid chamber is associated with a heater and cooler for the fluid chamber; more preferably, the heaters and the coolers comprise a thermoelectric heat pump attached to a heat sink having a heater element. Preferably, the heaters and the coolers can change the temperature of a fluid chamber at a rate of at least about 5° C. per second.

Additionally, each embodiment of the invention can further comprise (o) a permanent magnet that can be positioned adjacent to one or more of the fluid chambers, or removed therefrom, wherein further the invention comprises means for moving the magnet adjacent to or away from the cassette.

Each embodiment of the invention can also comprise (p) a detection chamber or channel having a transparent wall. Further, each such embodiment can include (q) a light source capable of directing light to the transparent wall of a chamber or channel; and also (r) a light detection device capable of detecting:

(1) the light reflected from an illuminated chamber or channel having a transparent wall;

(2) the light transmitted through an illuminated chamber or channel having a transparent wall; or (3) the light emissions emanating from an excited molecule in a chamber or channel having a transparent wall.

In a preferred embodiment, the invention includes at least one valve that comprises:

(1) a shut-off means comprising a valve ball or pinch foot, and (2) switching means for positioning the valve ball or pinch foot so that the valve ball or pinch foot: (i) presses against the flexible film to cut off flow through a first or second fluid exchange channel, or (ii) releases away from the flexible film to allow flow through the first or second fluid exchange channel. The switching means preferably comprises spring loaded levers. Preferably, at least one valve comprises:

(1) a spacer, (2) a spacer spring means for normally pressing the spacer against the flexible film so as to cut off the flow of fluids through a first fluid exchange channel, and (3) an electromagnet effective when activated to sufficiently release the pressure against the flexible film to allow the flow of fluids through the first or second fluid exchange channel.

In a preferred embodiment, the invention provides a device for conducting assays in parallel using fluids that are confined to a disposable cassette comprising the disposable assay cassette, which comprises (i) at least two reaction flow-ways, including a first reaction flow-way designed to receive and assay an experimental sample and a second reaction flow-way designed to receive and assay a negative control, (ii) for each reaction flow-way, at least one supply chamber connected thereto and containing fluids needed in the assay and at least one reaction chamber, (iii) a negative control supply chamber connected with the second reaction flow-way containing the negative control, and (iv) a test sample supply chamber connected with the first reaction flow-way designed to receive a test sample through an inlet connected with the test sample supply chamber, valves for controlling the flow of fluids in the cassette, and an instrument comprising a temperature control unit for controlling in parallel the temperature in a reaction chamber in each reaction flow-way, valve actuators for opening and closing the valves in the cassette, and one or more pumps for pushing fluid out of the various supply chambers and reaction chambers of the cassette. Preferably, the cassette further comprises (v) a third reaction flow-way designed to receive and assay a test sample and a positive control, (vi) connecting routes between the test sample supply chamber and both the first and third reaction flow-ways, wherein these connecting routes are controlled by valves that allow selective flow between the test sample supply chamber and either the first or third reaction flow-way, and (vii) a first positive control supply chamber connecting with the third reaction flow-way containing the positive control. Also preferably, the cassette further comprises (viii) a fourth reaction flow-way designed to receive and assay a positive control, and (ix) a second positive control supply chamber connecting with the fourth reaction flow-way containing the positive control. As well, the cassette preferably comprises (v) a third reaction flow-way designed to receive and assay a test sample and a positive control, (vi) connecting routes between the test sample supply chamber and both the first and third reaction flow-ways, wherein these connecting routes are controlled by valves that allow selective flow between the test sample supply chamber and either the first or third reaction flow-way, and (viii) a first positive control supply chamber connecting with the third reaction flow-way containing the positive control. Preferably, the pumps comprise one or more foot-pad pumps. Further, the temperature control unit preferably comprises a thermoelectric heat pump; and the thermoelectric heat pump preferably is attached to a heat sink having a heater element. Preferably, the valves of this embodiment comprise plunger-type valves.

The invention further provides a method of conducting assays, including chemical diagnostic assays, antibody-based assays and nucleic acid amplification-based assays, using one of the aforementioned devices, which method comprises (a) providing the device for conducting assays in parallel, wherein reagents and control materials are pre-loaded into the supply chambers;

(b) inserting a test sample into the test sample supply chamber; and (c) reacting in parallel in separate reaction flow-ways (1) the test sample and (2) the negative control.

Preferably, the reagents or control materials include binding domains derived from antibodies; alternatively, the reagents or control materials include fluids containing primers, nucleotide triphosphates, and ions and buffers suitable for supporting a nucleic acid amplification reaction. Preferably, the reacting comprises reacting in separate reaction flow-ways (1) test sample and (2) negative control with a suspension of nucleic acid-binding beads, wherein the suspension of nucleic acid-binding beads is provided by a separate supply chamber for each reaction flow-way; and replacing the fluid suspending the nucleic acid-binding beads with a fluid containing primers, nucleotide triphosphates, and ions and buffers suitable for supporting a nucleic acid amplification reaction. Preferably, the nucleic acid binding beads are paramagnetic beads and the replacing step comprises (1) magnetically locking the nucleic acid-binding beads in place while pushing the suspending fluid into a waste chamber, (2) resuspending the nucleic acid-binding beads in a wash fluid, wherein wash fluid is introduced from a separate supply chamber for each reaction flow-way, (3) magnetically locking the nucleic acid-binding beads in place while pushing the suspending fluid into a waste chamber, and (4) resuspending the nucleic acid-binding beads in the fluid containing primers, nucleotide triphosphates, and ions and buffers suitable for supporting a nucleic acid amplification reaction.

In a preferred embodiment, the invention relates to a method of conducting nucleic acid amplification reactions using the aforementioned device, which method comprises (a) providing the device for conducting assays in parallel, wherein reagents and control materials are pre-loaded into the supply chambers, wherein the reagents or control materials include primers, nucleotide triphosphates, and ions and buffers suitable for supporting a nucleic acid amplification reaction;

(b) inserting a test sample into the test sample supply chamber; and (c) reacting in parallel in separate reaction flow-ways (1) the test sample, (2) a negative control and (3) a mixture of the test sample and a positive control. The present invention further preferably relates to a method of conducting nucleic acid amplification reactions using the aforementioned device, which method comprises:

(a) providing the device for conducting assays in parallel, wherein reagents and control materials are pre-loaded into the supply chambers, wherein the reagents or control materials include primers, nucleotide triphosphates, and ions and buffers suitable for supporting a nucleic acid amplification reaction;

(b) inserting a test sample into the test sample supply chamber; and (c) reacting in parallel in separate reaction flow-ways (1) the test sample, (2) a negative control, (3) a mixture of the test sample and a positive control and (4) a positive control.

The invention still further provides a device comprising a cassette suitable for conducting reactions therein, which cassette comprises a body having one or more recesses and one or more embossed films covering the recesses.

Preferably, the cassette includes a hole extends through the body, further comprising a fluid exchange channel in communication with a valve, which valve is in communication with the hole, and a film having an embossed portion sealed to the body such that the hole and the fluid exchange channel are covered. The device further comprises preferably a pneumatically driven plunger for pressing the embossed film portion at or about the valve, and pressure control means for (i) applying a positive pressure to the pneumatically driven plunger such that the plunger presses against the flexible film so as to close the valve, and (ii) releasing the positive pressure to the pneumatically driven plunger such that the plunger releases from the flexible film so as to open the valve.

DEFINITIONS

Figure 1A:
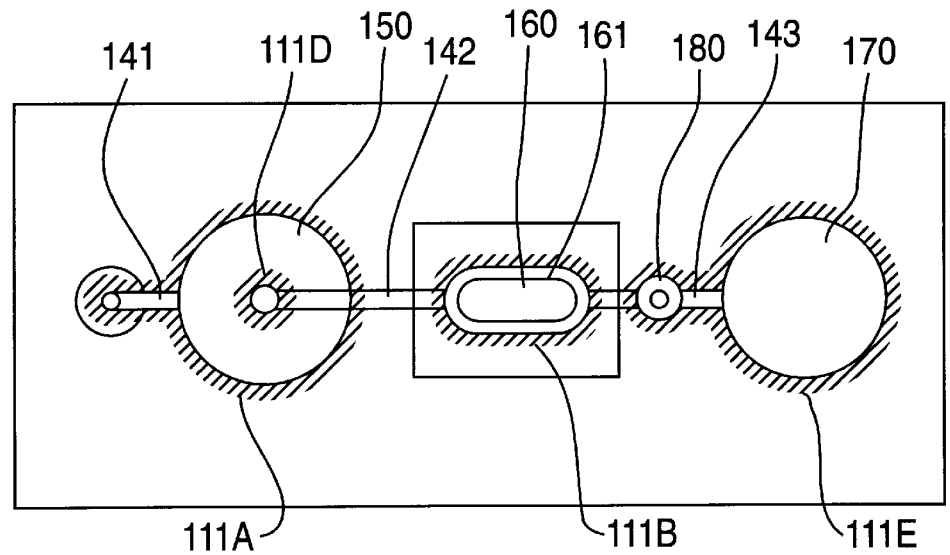
FIGS. 1A, 1B and 1C show a top, side and bottom view of a cassette of the invention.

The following terms used in this disclosure shall have the meanings set forth below:

annealing temperature

PCR protocols and other nucleic acid amplification protocols often use an "annealing temperature" less than the replication temperature to accelerate the rate at which the primers bind to (i.e., hybridize with) the sample nucleic acid; this annealing temperature is typically between about 45° C. and about 72° C., often about 55° C. Generally, the annealing temperature will be about 5° C. below the lowest $T_m$ for the interaction between (a) one of the primers used in reaction and (b) the target nucleic acid segment.

Bursapak chamber a chamber formed in a solid support and having a film formed of a flexible material that is sealed to the support at the edges of the chamber and has an outlet channel that is blocked by a portion of the film which is sealed over the outlet channel, wherein the seal over the outlet is broken or removed by pressurizing the fluid contents of the chamber at a pressure that does not affect the seal at the edges of the chamber; preferably, the film is on one face of the cassette body and the outlet is oriented toward the other.

cassette a disposable device for conducting reactions therein having a cassette body, one or more upper membranes or one or more lower membranes which individually or in combination define one or more supply chambers, one or more reaction chambers and fluid exchange channels connecting the supply chambers to reaction chambers.

cassette body a solid portion having sufficient depth and sturdiness to allow cavities formed therein to provide the depth for fluid chambers and fluid exchange channels.

collapsible upon evacuation some of the chambers described below will preferably be filled by first applying a vacuum to evacuate the chamber contents and then filling the evacuated chamber with fluid—preferably, these chambers are "collapsible" in that they have at least one flexible film that collapses to minimize chamber volume.

connection (between fluid chambers, inlets or detection channels)

two fluid chambers, inlets or detection channels are "connected" or have a "route of connection" therebetween if there is one or more fluid exchange channels joining the two such that fluid can move from one to the other.

concentric Bursapak supply chamber an internal outlet Bursapak supply chamber wherein the outlet channel is located substantially in the center of the supply chamber; "substantially in the center" means that the distance between the center of the supply chamber and the geometric center of the supply chamber is no more than about 20% of the length of the supply chamber cross-section defined by the line joining the center of the outlet and the geometric center of the supply center.

DNA strand separation temperature the temperature used in a nucleic acid amplification protocol to separate the complementary strands of nucleic acid that may be present in a sample; this temperature is typically between about 92° C. and about 97° C., preferably about 94° C.

elevated pressure a pressure more than ambient atmospheric pressure.

fillable from a vacuum-collapsed state to a defined volume these are chambers that unfold from the collapsed state to a first volume;

preferably, the inserted fluid volume is within about 10% of the first volume, more preferably within about 3% of the first volume. The first volume is the maximum volume of fluid that can be inserted into the chamber without affecting the integrity of the chamber.

fluid chamber the term "fluid chamber" encompasses reaction, supply, waste metering and sample storage chambers, and other fluid containing chambers. In those embodiments where contents of the chambers can be pumped out using a foot-pad having a shape that conforms to a covering film that is inverted to match the shape of the bottom of the chamber, the chamber can be closed by maintaining the foot-pad pressed against the inverted covering film.

fluid-tight a space or chamber is fluid-tight if it retains an aqueous fluid in the space at a temperature of 99° C. for one hour; a seal between two materials is fluid-tight if the seal is substantially no more permeable to water than the most water-permeable such material.

foot-pad a plunger having a shape designed to conform to the inverted shape of the covering film of a supply chamber; when the plunger presses against the flexible film it pressurizes the fluid in the supply chamber and, if an exit is available, pushes the fluid out of the supply chamber.

foot-pad pump a mechanical, electromechanical or pneumatic device that uses a one or more, preferably two or more, foot-pads to press on one or more fluid chambers such as supply chambers or reaction chambers to pressurize the contents and push the contents out through an unobstructed connected fluid exchange channel.

integral parts or elements of a valve are integral to a body layer or to a cassette if They cannot be facilely and reversibly detached from that body layer or cassette.

internal outlet Bursapak supply chamber a Bursapak supply chamber wherein the outlet channel is located away from the edges of the supply chamber such that fluid-containing space is interposed between the sealed outlet channel and the edges chamber.

negative control a material designed to be comparable to a sample to be assayed but lacking the substance to be assayed for, such that a positive result upon assaying a negative control would indicate a problem with the assay protocol or assay reagents.

nucleic acid melting temperature or $T_m$ the transition temperature for two-stranded duplex of nucleic acid at which the equilibria shifts from favoring the base-paired duplex to favoring the separation of the two strands.

positive control a material designed to generate, in the absence of a problem with the assay chemistry such as the presence of an interfering substance, a positive assay result.

reaction flow-away a series of two or more serially connected fluid chambers through which fluids can move.

reduced pressure a pressure less than ambient atmospheric pressure.

replication temperature the temperature used in a nucleic acid amplification protocol to allow the nucleic acid reproductive enzyme to reproduce the complementary strand of a nucleic acid to which a primer is bound (i.e., hybridized); this temperature is typically between about 69° C. and about 78° C., preferably about 72° C., when using a heat stable polymerase such as Taq polymerase.

serially connected two or more fluid chambers are serially connected if there are fluid exchange channels by which fluid from a first of the serially connected chambers can pass to a second of the serially connected chambers, and from there to a third of the serially connected chambers, and so on until the fluid passes to the last of the serially connected chambers.

substantially uniform temperature in the reaction chamber where the temperature in a reaction chamber varies by no more than about ±0.3° C.

target nucleic acid segment a segment of nucleic acid that is sought to be identified or measured in a sample, such as a sequence intended, if present, to be amplified in a nucleic acid amplification reaction such as a PCR reaction, strand displacement assay or ligase chain reaction; the target segment is typically part of a much larger nucleic acid molecule found in the sample.

thermoelectric heat pump a device for heating and cooling fluid chambers that is made up of one or more thermoelectric blocks.

DETAILED DESCRIPTION

The cassette of the present invention includes at least one reaction chamber and at least one supply chamber in combination with interconnecting fluid exchange channels. The cassette comprises a body into which the aforementioned chambers and channels are formed such that when covered by a film and sealed, as described below, the formed body with film can hold fluids. The shape of the body can be any shape, although preferably it is a flat square, rectangular or circular structure of length and width or diameter substantially greater than its depth, such as, for example, 3 cm×3 cm×3 mm, inter alia, and the length and width or diameter can be further described with respect to a top or bottom surface, and the depth can be further described with respect to an edge. The chambers and channels prior to covering by the film can be open to any surface of the body, preferably is open to the top or bottom, more preferably is open to the top and bottom, although each chamber or channel preferably is open to one side only.

The present invention is described herein with respect to particular embodiments; however, these embodiments should not be construed as in any way limiting the scope of the present invention, which includes all modifications encompassed within the spirit and scope of the invention as described hereinbelow.

Exemplary Cassette

Figure 1B:
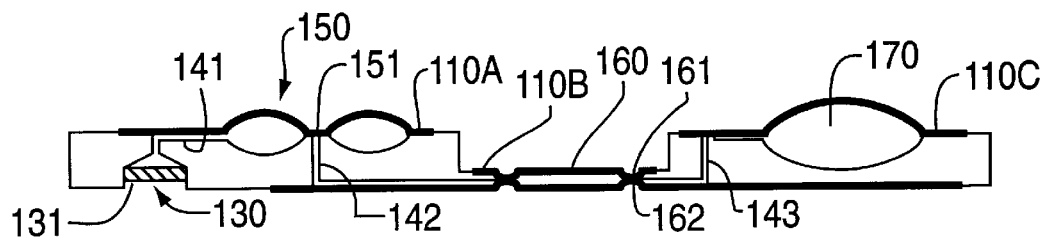
Figure 1C:
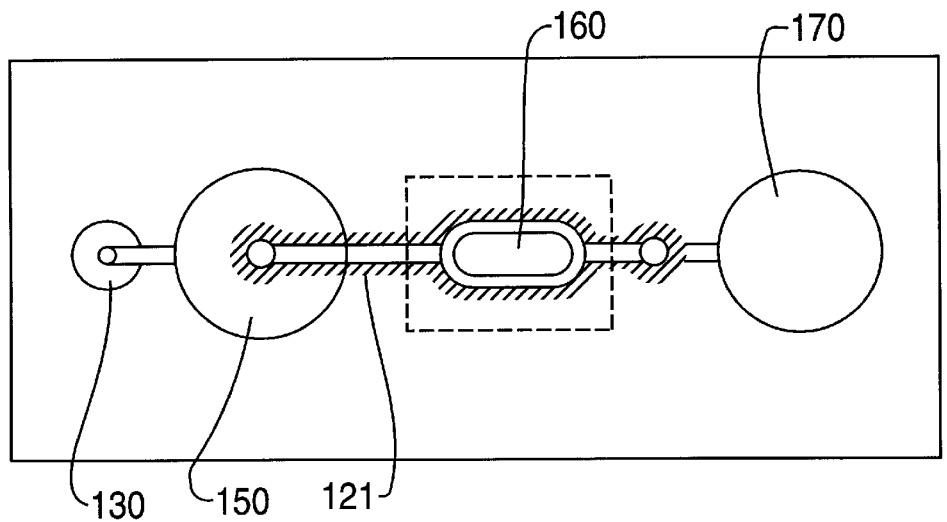

FIGS. 1A, 1B and 1C show a top view, cross-sectional view and bottom view of a portion of one embodiment of a cassette 100 according to the invention. The cassette 100 has a body 105 in which are defined inlet 130, first fluid exchange channel 141, supply chamber 150, second fluid exchange channel 142, reaction chamber 160, third fluid exchange channel 143 and waste chamber 170. The body 105 has first upper film 110A, second upper film 110B, third upper film 110C and lower film 120. In FIG. 1A, first seal portion 111A (shaded area), second seal portion 111B (shaded area) and third seal portion 111C (shaded area) show where first upper film 110A, second upper film 110B and third upper film 110C, respectively, are sealed against body 105. In FIG. 1C, shading 121 shows where lower film 120 is sealed against body 105. Inlet 130 has a septum 131. First, second and third upper films 110A–C are collectively referred to as "upper films 110." Septum 131 can be, for instance a bilayer material formed of an outer layer of silicon or neoprene rubber and an inner layer of chemically inert material such as tetrafluoroethylene homopolymer (e.g., Teflon, E. I. duPont de Nemours and Co., Wilmington, Del.) facing the body 105. Second upper film 110B and lower film 120 are embossed or shaped at positions 161 and 162 to help form reaction chamber 160, as will be described in greater detail below with reference to FIGS. 11A and 11B. First upper film 110A is embossed or shaped at the location of supply chamber 150 so that first upper film protrudes above the upper surface of body 105, creating a greater volume for supply chamber 150 and facilitating the mechanism by which supply chamber 150 is emptied, as described further in the text below with reference to FIGS. 2A and 2B. Third upper film 110A is embossed or shaped at the location of waste chamber 170, which embossing facilitates the mechanism by which the waste chamber is filled. A valve 180 is formed in third fluid exchange channel 143. The outlet 151 of supply chamber 150 is sealed by a portion of first upper film 110A. Supply chamber 150 is a Bursapak supply chamber, which type of supply chamber is a particularly useful type of supply chamber for use in the cassette of the invention. Because many of the cassettes described below make use of this preferred type of supply chamber, Bursapak supply chambers are described in more detail in the following section.

Bursapak Supply Chambers

Figure 2A:
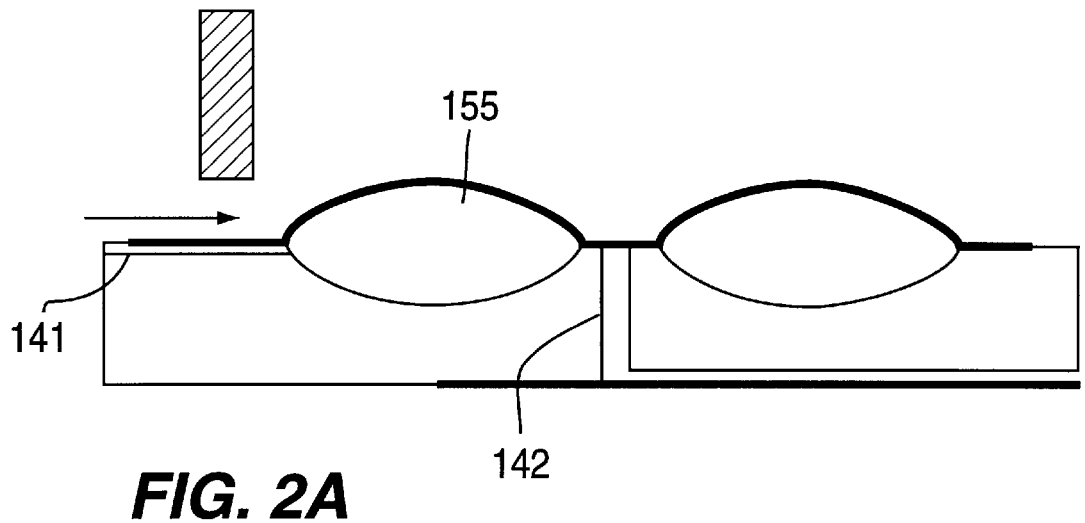
FIG. 2A shows a side view of a Bursapak supply chamber.
Figure 2B:
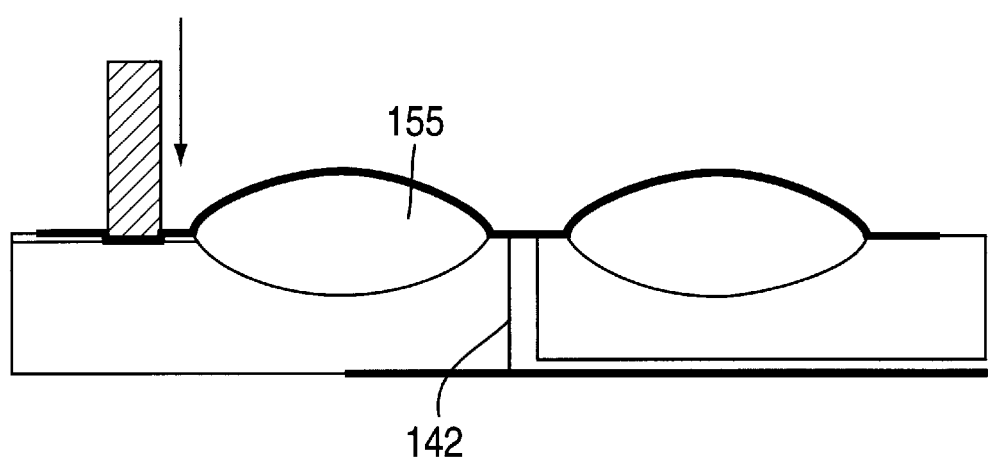
FIG. 2B illustrates a method for sealing closed a fluid exchange channel.
Figure 2C:
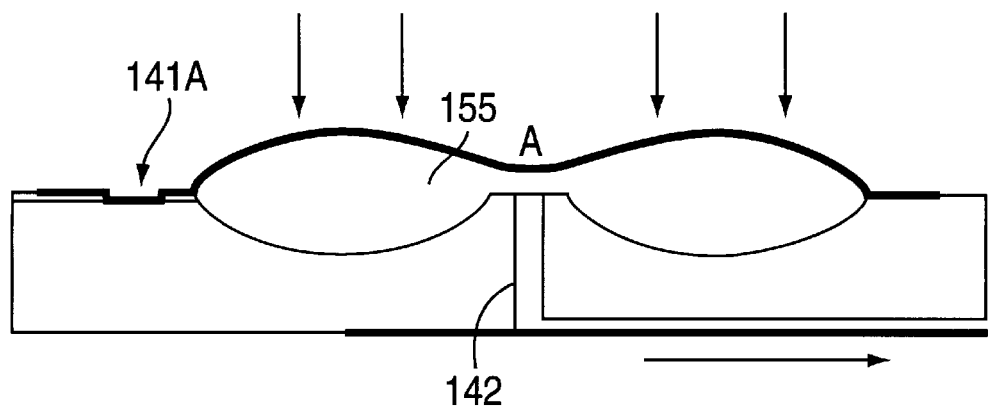
FIG. 2C illustrates how pressure can be used to open a Bursapak supply chamber.
Figure 2D:
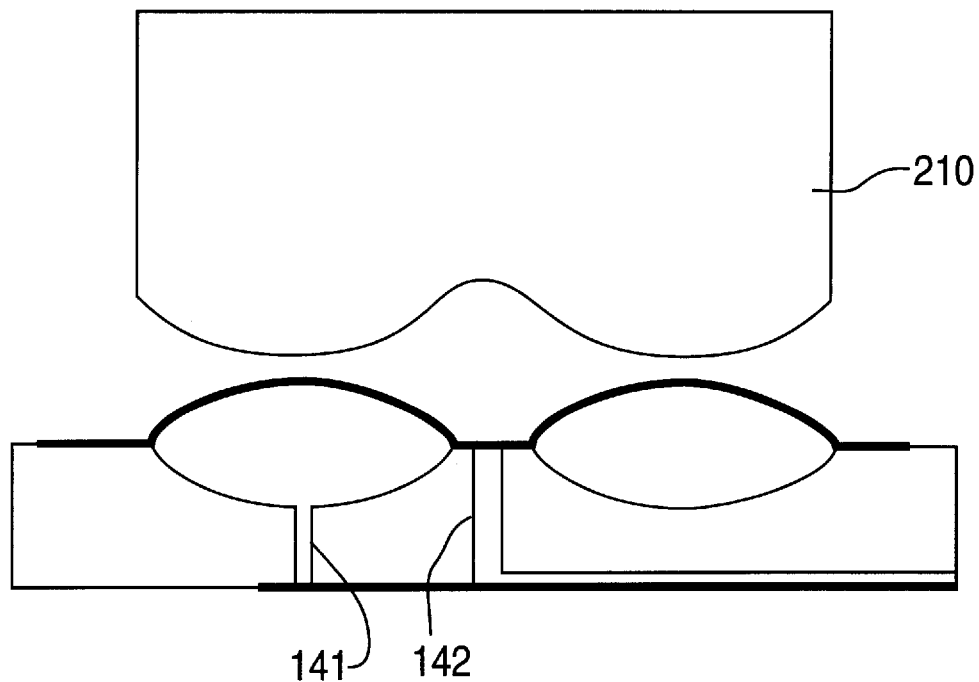
FIGS. 2D and 2E illustrate a foot-pad that can be used to pressurize the fluid in the Bursapak supply chamber.
Figure 2E:
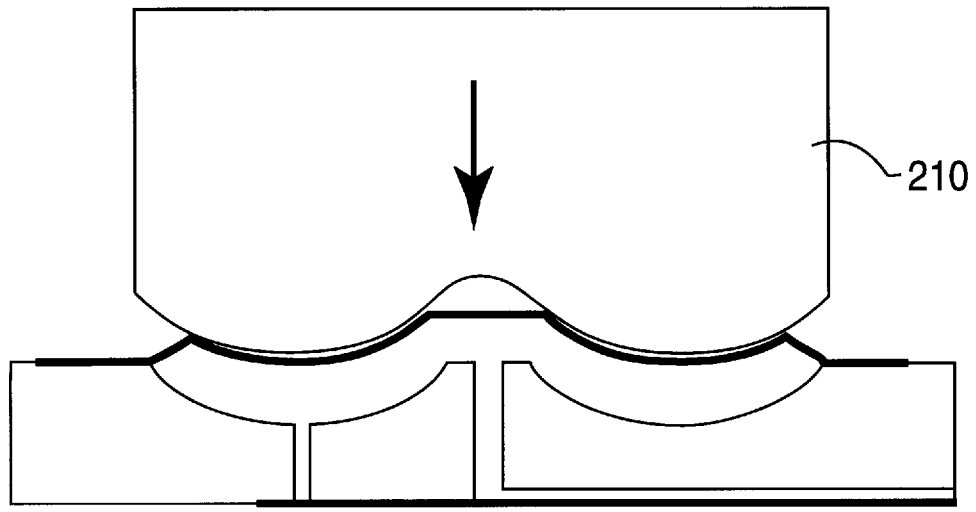

FIG. 2A shows a side view of a Bursapak supply chamber 150 having supply cavity 155, which can contain a fluid. The Bursapak supply chamber 150 has an inlet first fluid exchange channel 141, which is preferably sealed, for instance by heat sealing at sealing location 141A, after the Bursapak supply chamber 150 has been filled with fluid, and an outlet second fluid exchange channel 142 which is initially sealed with a fourth seal portion 111D of first upper film 110A. FIG. 2B shows the use of die 1300 to heat seal first fluid exchange channel 141, at sealing location 141A. FIG. 2C illustrated how pressure—indicated by the arrows—applied to the fluid in Bursapak supply chamber 700 is effective to pull the seal portion 111 away from the outlet second fluid exchange channel 142. FIG. 2D illustrates a foot-pad 210 that can be used to apply pressure to the fluid in Bursapak supply chamber 150 and pump it through outlet second fluid exchange channel 142. Foot-pads can be fabricated of any suitably sturdy material including, without limitation, aluminum, plastics, rubber, alumina, copper, sintered beryllia, and the like. Upper films 110 and lower films 120 are preferably constructed of a flexible film such as a polyethylene, polyvinylidene fluoride or polyethylene/polyethylene terephthalate bi-layer film. Suitable films are available from Kapak Corporation, Minneapolis, Minn. or E. I. duPont de Nemours and Co., Wilmington, Del. Polyethylene/polyethylene-terephthalate bi-layer film such as 3M No. 5 or 3M No. 48 (3M Corp., Minn.) or Dupont M30 (DuPont de Nemours, Wilmington, Del.) are particularly preferred. The polyethylene layer is preferably positioned against body 105. FIG. 2E shows the foot-pad used to pump fluid out of Bursapak supply chamber 150.

The first upper film 110A is embossed or shaped, for instance by applying suitably shaped, heated dies to the first upper film 110A, so that it can protrude away from the body 105 when the supply chamber 150 is filled and will rest, without substantial stretching, against the bottom of supply chamber 150 when the supply chamber 150 is evacuated.

It is believed that the application of force through a foot-pad results in the application of greater force per unit length at the edges of the fourth seal portion 111D than at the edges of first seal portion 111A, resulting in selective peeling of fourth seal portion 111D. Whatever the mechanism, however, in operation Bursapak chambers operate as illustrated in FIGS. 2A–2C. To assure proper functioning, in some embodiments it may be necessary to seal fourth portion 111D relatively more weakly, for instance using a weaker adhesive or a lower temperature sealing die.

Materials, Dimensions for Cassette Components

Body 105 is preferably formed of a molded plastic, such as high density polyethylene, but other materials that are suitably resistant to the chemistries sought to be conducted on the parallel reaction device, such as glass and silicon-based materials, can be used. Where body 105 is plastic, it is preferably formed by a molding process that is used to form cavities and channels that will be sealed with upper and lower films 110 and 120 to form fluid chambers and fluid exchange channels. Such cavities and channels are formed in glass and silicon materials by chemical etching or laser ablation. Upper and lower films 110 and 120 typically have a thickness of from about 0.3 mils to about 5 mils, preferably from about 1 mil to about 3 mils. For fluid chambers having a diameter of about 1 cm or more, the film thickness is more preferably about 2 mils. Reaction chamber 130A typically has a thickness, between upper and lower films 110 and 120, of from about 0.1 mm to about 3 mm preferably of from about 0.5 to about 1.0 mm and an area, defined by the inner surface of upper or lower films 110 or 120, of preferably from about 0.05 $cm^2$ to about 2 $cm^2$, more preferably from about 0.1 $cm^2$ to about 1 $cm^2$, yet more preferably about 0.5 $cm^2$. The dimensions of reaction chamber are preferably sized small enough to permit rapid thermal cycling (on the order of about 10 seconds).

Fluid exchange channels typically have a diameter between about 200 and about 500 $\mu$m. Supply chambers 150 typically have a volume between about 5 and about 500 $\mu$l, preferably from about 10 to about 200 $\mu$l, more preferably from about 30 to about 160 $\mu$l. Metering chambers preferably have a volume between about 5 and about 50 $\mu$l. Preferably, the total volume of each reaction chamber 160 is between about 5 $\mu$l and about 200 $\mu$l, more preferably, between about 10 $\mu$l and about 100 $\mu$l. Preferably, each reaction chamber has a thickness (i.e., distance between upper film 110 and lower film 120) of about 1 mm or less.

Upper and lower films 110 and 120 preferably are resistant to temperatures as high as about 120° C. and are between about 1 and about 6 mils in thickness, more preferably, between about 2 and about 4. The thinness of the membranes facilitates rapid heat exchange between the reaction chamber and an adjacent heating or cooling device.

Schematic of Parallel Reaction Device

Figure 3:
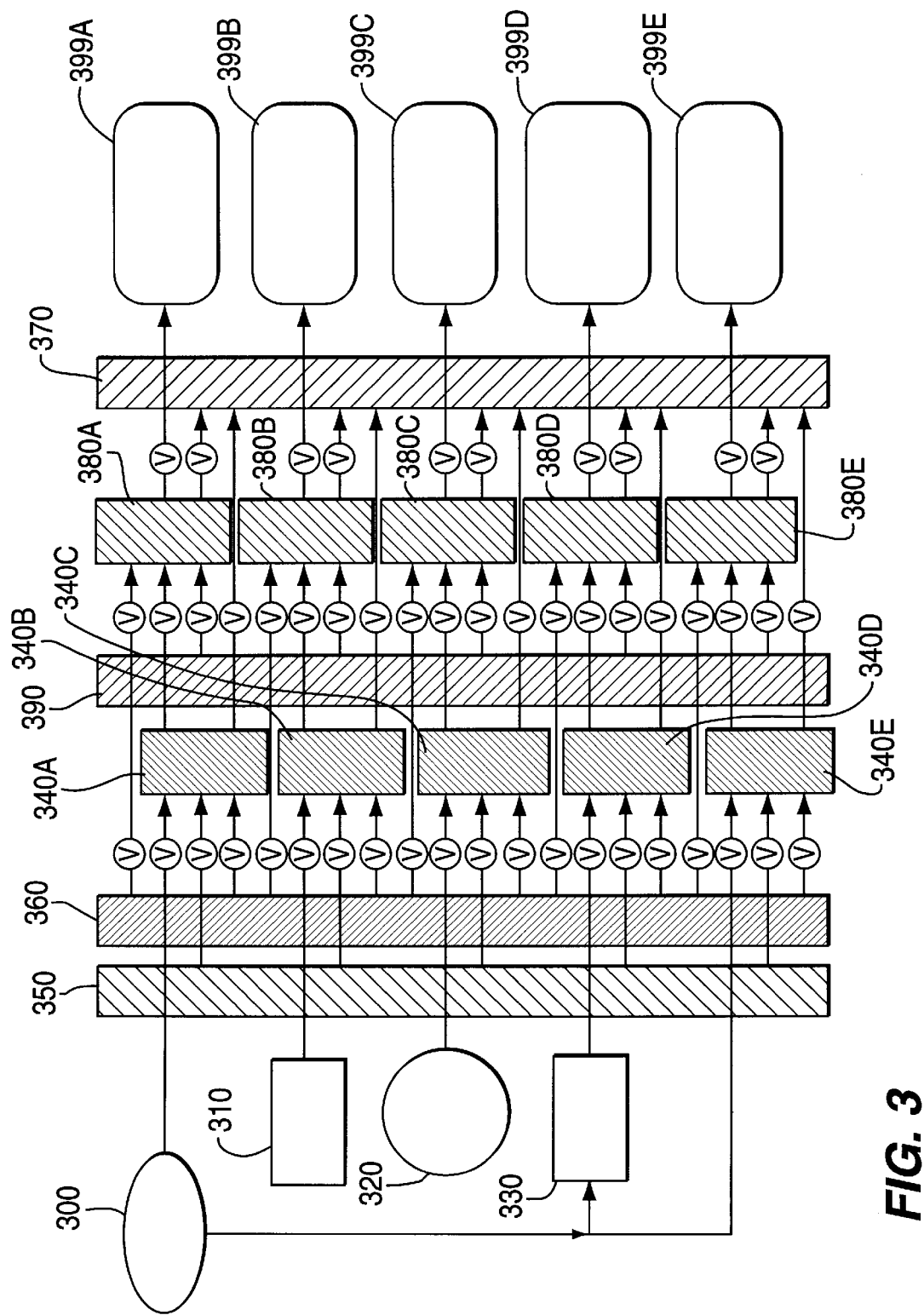
FIG. 3 schematically diagrams a parallel reaction device of the invention.

FIG. 3 illustrates schematically a parallel reaction device 301 according to the invention having five reaction flow-ways, each such flow-way, respectively, used for analyzing (A) a sample 300, (B) a positive control 310, (C) a negative control 320, (D) a positive control 330 combined with sample 300, and (E) a sample 300. Each of these samples and controls is introduced into one of first through fifth lysing chambers 340A–E (collectively, lysing chambers 340). Lysing reagents and washing buffer can be distributed from first supply chamber 350 and second supply chamber 360, respectively, to all five lysing chambers 340. Waste can be emptied from lysing chambers 340 into a single waste chamber 370. The remaining contents of each of lysing chambers 340 can then be transferred to one of first through fifth reaction chambers 380A–E, respectively (collectively, reaction chambers 380). Amplification reagents are added to each of reaction chambers 380 from a third supply chamber 390. Waste can be emptied from reaction chambers 380 into waste chamber 370. The remaining contents of each of reaction chambers 380A–E can then be transferred into one of first through fifth storage chambers 399A–E, respectively. Each valve which regulates the flow of fluids into and out of the various chambers is separately diagrammed in FIG. 3 as an encircled letter "v."

It should be noted that some of the arrows in FIG. 3, which arrows represent fluid channels, apparently pass through a fluid chamber. These channels actually pass above or below the fluid chamber, as is described further in the text below. As is described further below, lysing chambers 340 and reaction chambers 380 preferably have flexible upper film 110 and lower film 120 that can be manipulated with a foot-pad pump or a gas pressure flow control means. If both upper and lower walls of a fluid chamber are formed with films 110 and 120, then channels passing through the region of the device occupied by the lysis chambers 340 or reaction chambers 380 must pass adjacent to such chambers rather than above or below the chambers.

Detailed Cassette—Structure

Figure 4A:
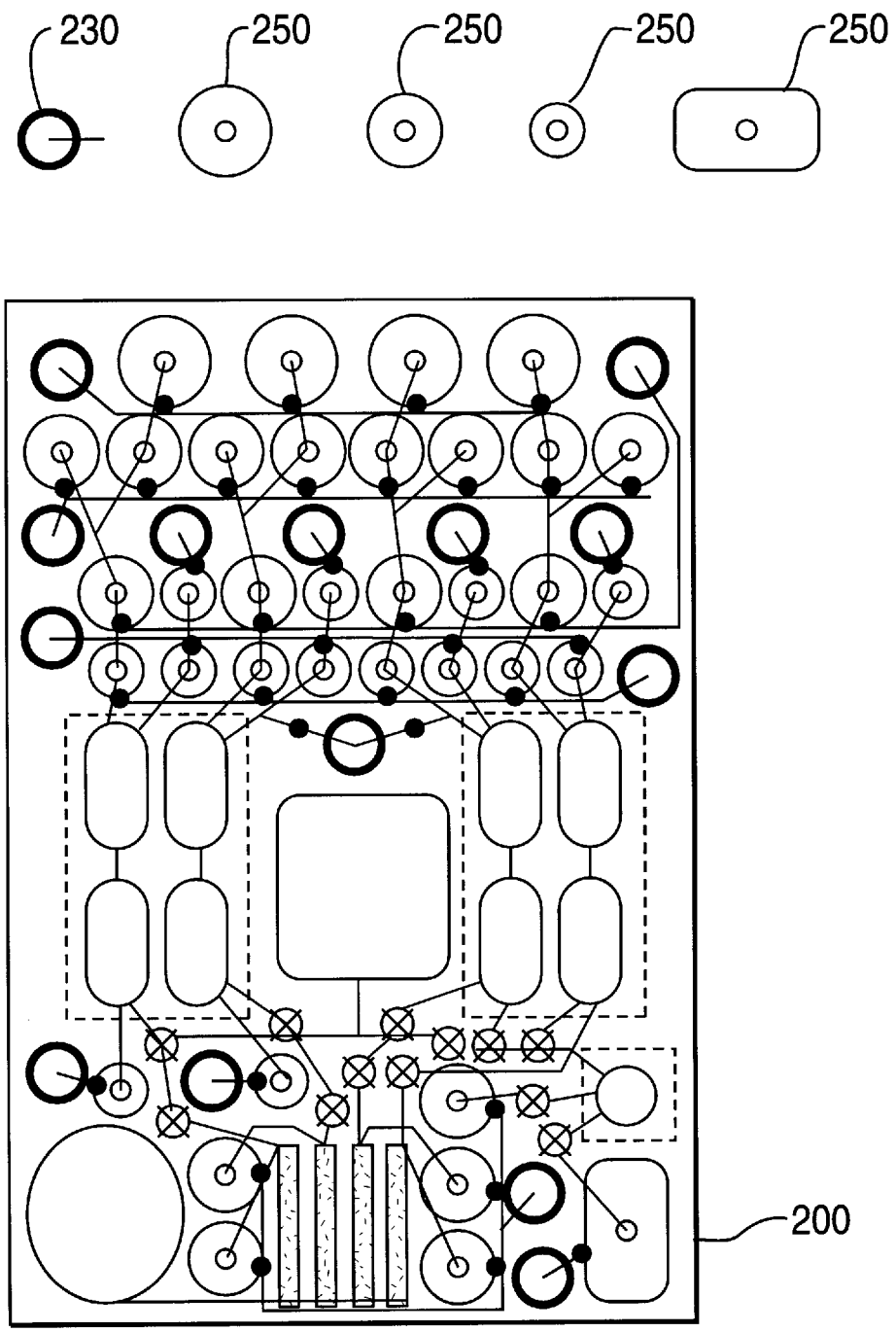
FIG. 4A illustrates a cassette of the invention.
Figure 4B:
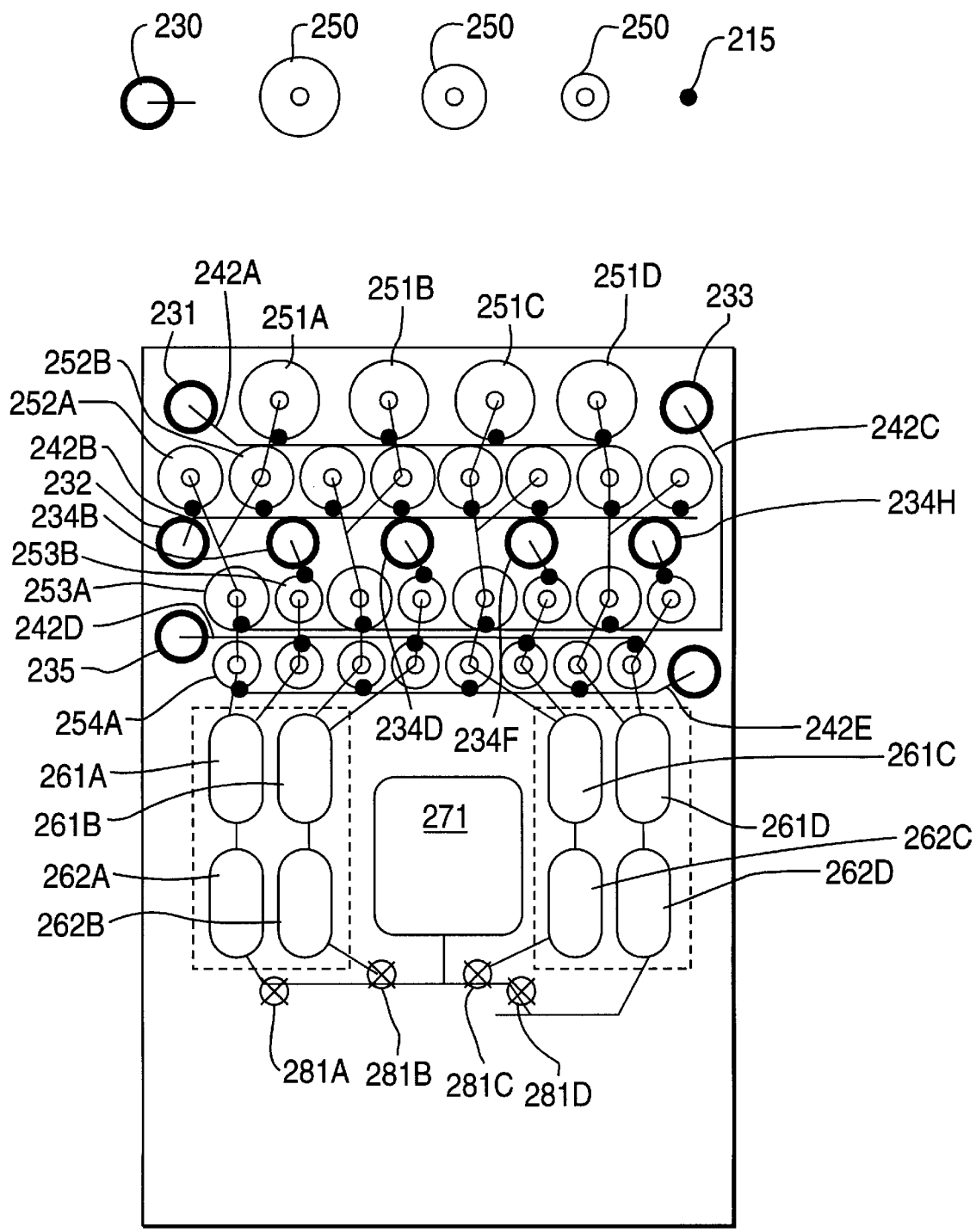
FIGS. 4B–4E show the cassette of FIG. 4A with various subsets of the features thereof illustrated and numbered.

Another cassette 200 is illustrated in FIG. 4A. The illustrated cassette 200 has planar dimensions of 3¼ inches by 5⁵⁄₁₆ inches, although other sizes are contemplated, including for instance in circumstances where the sizes of the fluid chambers and other components of the cassette differ from those illustrated. Because of the complexity of FIG. 4A, FIGS. 4B–4E show the body 205 of the cassette together with illustrations of various subsets of the components of body 205. In these illustrations the solid lines connecting inlets, valves or fluid chambers represent fluid exchange channels. Those fluid exchange channels represented by dark lines are formed in the upper surface of body 205, while those represented by lighter lines are formed in the lower surface of body 205. At the top of FIG. 4B are illustrated the symbols used to represent an inlet 230 or a supply chambers 250 of various sizes (sizes recited for illustrative purposes only).

In FIG. 4B are illustrated: alpha first supply chamber 251A, beta first supply chamber 251B, and so on through delta first supply chamber 251D, which are connected to first inlet 231 by alpha second fluid exchange channel 242A; alpha second supply chamber 252A, beta second supply chamber 252B, and so on through theta second supply chamber 253H, which are connected to second inlet 232 by beta second fluid exchange channel 242B; alpha third supply chamber 253A, beta third supply chamber 253B, and so on through theta third supply chamber 253H, of which alpha, gamma, epsilon and eta third supply chambers 253A, C, E and G are connected to third inlet 233 by gamma second fluid exchange channel 243B and beta, delta, zeta and theta third supply chambers 253B, 253D, 253F and 253H are connected to beta fourth inlet 234B, delta fourth inlet 234D, zeta fourth inlet 234F and theta fourth inlet 234H, respectively; and alpha fourth supply chamber 254A, beta fourth supply chamber 254B, and so on through theta fourth supply chamber 254H, of which alpha, gamma, epsilon and eta fourth supply chambers 254A, 254C, 254E and 254G are connected to fifth inlet 235 by delta second fluid exchange channel 242D and beta, delta, zeta and theta fourth supply chambers 254B, 254D, 254F and 254H are connected to sixth inlet 236 by epsilon second fluid exchange channel 242E. The connecting fluid exchange channels 215 between second fluid exchange channels 242 and supply chambers 250 are represented by solid circles.

Alpha first reaction chamber 261A can receive fluid from any of seven supply chambers 250, which supply chambers 250 are alpha first supply chamber 251A, alpha second supply chamber 252A, beta second supply chamber 252B, alpha third supply chamber 253A, beta third supply chamber 253B, alpha fourth supply chamber 254A and beta fourth supply chamber 254B. Beta first reaction chamber 261B, gamma first reaction chamber 261C and delta first reaction chamber 261D each can receive fluid, in a manner parallel to the arrangement for alpha first reaction chamber 261A, from seven supply chambers 250 as illustrated. Alpha first reaction chamber 261A, beta first reaction chamber 261B, gamma first reaction chamber 261C and delta first reaction chamber 261D connect to alpha second reaction chamber 262A, beta second reaction chamber 262B, gamma second reaction chamber 262C and delta second reaction chamber 262D, respectively, via alpha first fluid exchange channel 241A, beta first fluid exchange channel 241B, gamma first fluid exchange channel 241C and delta first fluid exchange channel 241D, respectively. Alpha second reaction chamber 262A, beta second reaction chamber 262B, gamma second reaction chamber 262C and delta second reaction chamber 262D connect to first waste chamber 271 under the control of alpha first valve 281A, beta first valve 281B, gamma first valve 281C and delta first valve 281D, respectively.

Figure 4D:
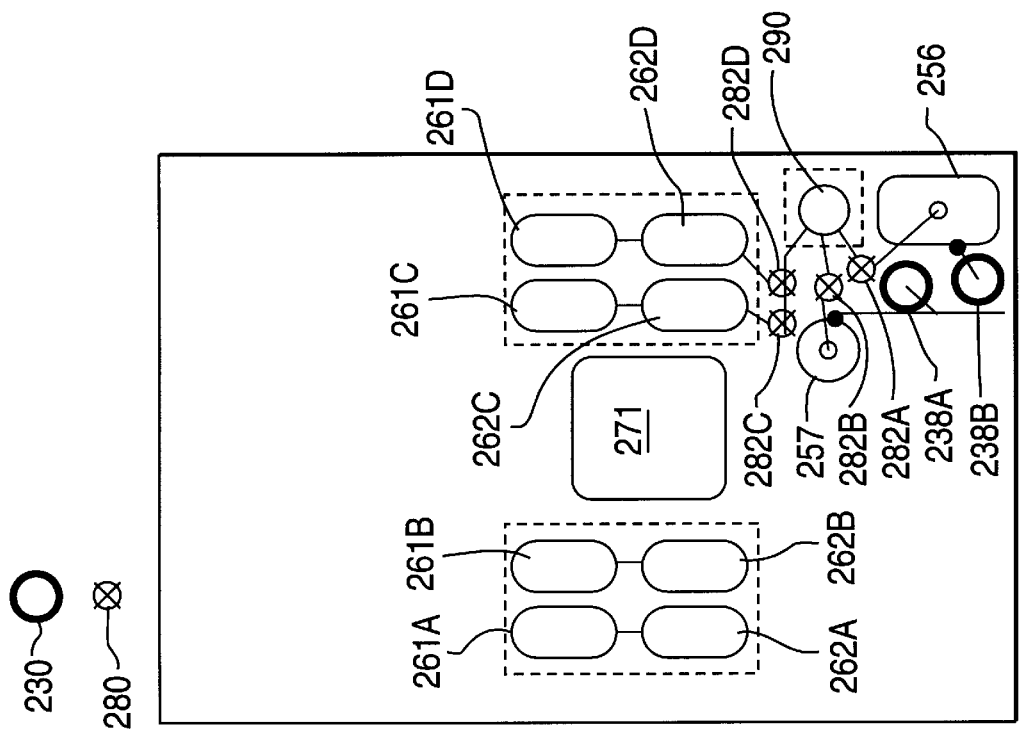
Figure 4C:
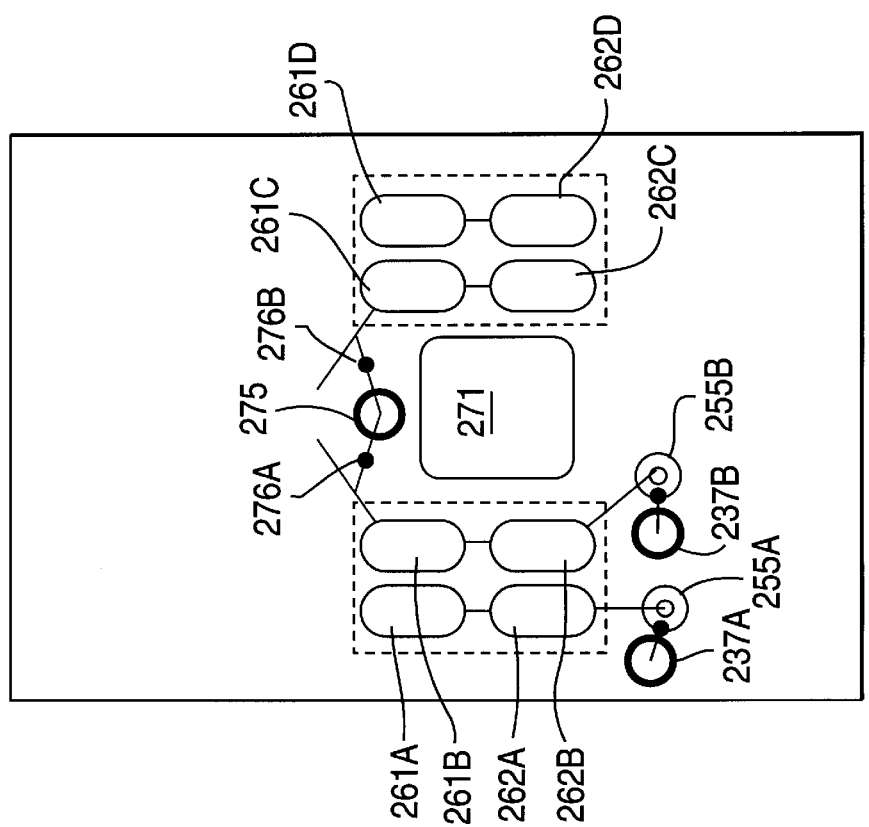

In FIG. 4C are illustrated alpha seventh inlet 237A and beta seventh inlet 237B, which are connected to alpha fifth supply chamber 255A and beta fifth supply chamber 255B, respectively. Alpha fifth supply chamber 255A and beta fifth supply chamber 255B are connected to alpha second reaction chamber 262A and beta second reaction chamber 262B.

Exhaust port 275 allows the first reaction chambers 261, second reaction chambers 262, first waste chamber 271, second waste chamber 272, metering chamber 290 and detection channels 295 to be evacuated prior to use. This evacuation is possible because all of the first reaction chambers 261, second reaction chambers 262, first waste chamber 271, second waste chamber 272, metering chamber 290 and detection channels 295 communicate when the appropriate valves 280 are open. Alpha sealing position 276A and beta sealing position 276B can be heat sealed when the evacuation process is complete to lock the first reaction chambers 261, second reaction chambers 262, first waste chamber 271, second waste chamber 272, metering chamber 290 and detection channels 295 in the evacuated state prior to operating the cassette.

In FIG. 4D, sixth supply chamber 256 is filled using alpha eighth inlet 238A and is connected to metering chamber 290 under the control of alpha second valve 282A. Seventh supply chamber 257 is filled using beta eighth inlet 238B and is connected to metering chamber 290 under the control of beta second valve 282B. From metering chamber 290 fluid can be directed to either gamma second reaction chamber 262C or delta second reaction chamber 262D under the control of gamma second valve 282C and delta second valve 282D, respectively.

Figure 4E:
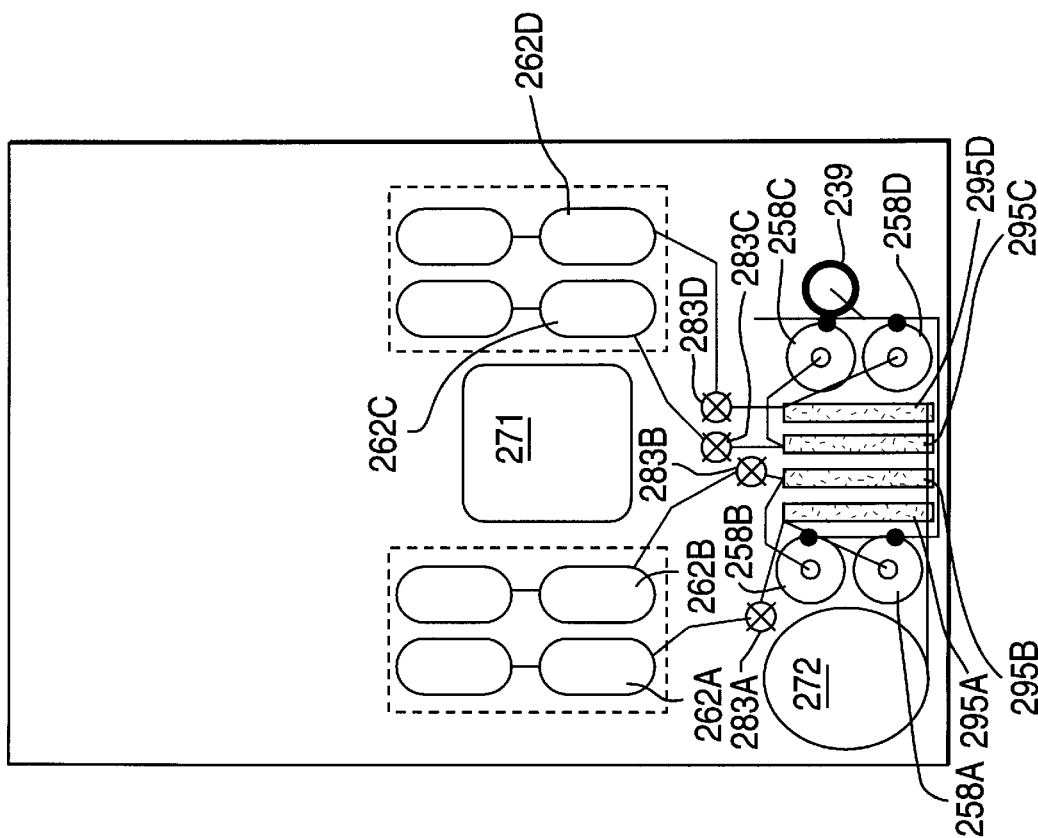

In FIG. 4E, fluid from alpha second reaction chamber 262A can be directed to alpha detection channel 295A under the control of alpha third valve 283A. Corresponding connections from beta second reaction chamber 262B through delta second reaction chamber 262D to beta detection channel 295B through delta detection channel 295D, respectively, are controlled by beta third valve 283B through delta third valve 283D, respectively. Alpha eighth supply chamber 258A, beta eighth supply chamber 258B, and so on, are respectively connected to alpha detection channel 295A, beta detection channel 295B, and so on. Alpha eighth supply chamber 258A, beta eighth supply chamber 258B, and so on are filled through ninth inlet 239.

Detailed Cassette—Operational Features

This discussion of operational features of the cassette structure 200 shown in FIGS. 4A–4E assumes that the supply chambers of that structure are Bursapak supply chambers. The first supply chambers 251 can be used to store fluid having suspended paramagnetic beads used in preparing nucleic acid from biological samples, which paramagnetic beads are described in greater detail below. A foot-pad pump operates propel in parallel the fluid and suspended beads from the first supply chambers 251 to the connected first reactions chambers 261. To assure that the beads are suspended the foot-pad pump operating on the first supply chambers 251 and foot-pad pump operating on the first reaction chambers 261 can alternately be operated to move the fluid back and forth between the first supply chambers 251 and first reaction chambers 261, thereby agitating the fluid and resuspending the beads.

The second supply chambers 252 can contain a buffer solution, such as a buffer solution used to wash the paramagnetic beads. The associated foot-pad pump has four foot-pads designed to interact with either (1) alpha second supply chamber 252A, gamma second supply chamber 252C, epsilon second supply chamber 252E and eta second supply chamber 252G or (2) beta second supply chamber 252B, delta second supply chamber 252D, zeta second supply chamber 252F and theta second supply chamber 252H. Alternatively, the pump has two sets of four pads designed to interact with second supply chambers 252.

The third supply chambers 253 alternate in size between supply chambers 253 having volumes of 100 μl and supply chambers 253 having volumes of 30 μl. The 100 μl supply chambers 253 can be used to store cell lysis solutions while the 30 μl supply chambers 253 can be used to store solutions of primers.

Alpha, gamma, epsilon and eta fourth supply chambers 254A, 254C, 254E and 254G can be used to store a solution containing the appropriate nucleotide triphosphates for a nucleic acid amplification assay. Beta, delta, zeta and theta fourth supply chambers 254B, 254D, 254F and 254H can be used to store solutions containing the polymerase enzyme for the nucleic acid amplification assay.

A desirable feature for a cassette such as that illustrated in FIGS. 4A–4E is the ability to incorporate a positive control in one or more, but not all, of the reaction flow-ways 265 (not identified in Figures, first reaction flow-way 265A includes alpha first and second reaction chambers 261A and 262A, second reaction flow-way 265B includes beta first and second reaction chambers 261B and 262B, and so on). Thus, a material that should generate a positive assay result can be inserted into sample that otherwise may or may not produce a positive signal (i.e., experimental samples) or in samples that should not produce a positive signal (i.e., negative controls). In this way, the source of any substances that interfere with the assay can be determined. Any failure of the reaction flow-ways containing a positive control to generate a positive signal or an appropriately strong positive signal would indicate that a standard solution used in the assay contains a substance or has a property that interferes with the assay. Fluids expected to generate negative signals can also be incorporated into the cassette.

Controls, e.g., fluids that have a predetermined amount of a component to be tested for or that are known to lack the component, can be inserted into alpha and beta second reaction chambers 262A and 262B from alpha and beta fifth supply chambers 255A and 255B. Note that this particular embodiment does not include a facile way to introduce both a positive control and a test sample into a reaction flow-way; however, modifications of the cassette 200 of FIGS. 2A–2E that would allow such a means of introduction are easily envisioned.

Not all Bursapak supply chambers 250 must be utilized. A Bursapak supply chamber is avoided simply by not pumping its contents into the connected reaction chambers.

It is desirable to contain all waste fluids in the cassette 200. Thus, the illustrated cassette 200 has a first waste chamber 271 and a second waste chamber 272 (collectively waste chambers 270) of sufficient volume to accommodate all the fluids introduced into the cassette. Waste chambers 270 are prepared in an evacuated state such that the films forming the outer wall of the waste chambers 270 (see film 110C of FIG. 1) rest against the inner surfaces of the waste chambers 270. As fluid is pumped into the waste chambers 270, the film will flex outwardly to provide room for the inserted fluid. It is desirable to confine the fluids to the cassette for instance to isolate biohazards or, in the case of nucleic acid amplification assays, to minimize the opportunity for aerosols to spread nucleic acid through the lab creating the potential for cross-contamination of other assays.

Supply chambers 250 are also evacuated in like manner prior to filling. Most supply chambers 250 will, in a preferred embodiment, be prefilled prior to shipment to the laboratory where the assay will be conducted. Of course, the test sample will be inserted at the lab site. Fluid insertion is best described with reference to FIG. 1B. A needle can be inserted into septum 131 and used to evacuate supply chamber 150, causing film 110A to collapse onto the floor of supply chamber 150. Then, fluid can be inserted through the septum into supply chamber 150. The first fluid exchange channel is then blocked, for instance by heat sealing or by crimping.

Focusing on delta reaction flow-way 265D, note that experimental sample from sixth supply chamber 256 is first relayed to delta second reaction chamber 262D while flow to delta first reaction chamber 261D is blocked by operating a foot-pad pump minimize the volume of delta first reaction chamber 261D. Typically, the first reaction conducted on the experimental sample will occur in delta first reaction chamber 261D. To move the experimental sample from delta second reaction chamber 262D to delta first reaction chamber 261D, delta second valve 282D is closed, the foot-pad pump acting on delta first reaction chamber 261D is released, and the foot-pad pump acting on delta second reaction chamber 262D is operated to pump the experimental sample into delta first reaction chamber 261D.

Foot-pad pumps that operate to drain a supply chamber 150 can remain engaged with the supply chamber 150 to prevent back-flow into the supply chamber 150.

Valves

Figure 5A:
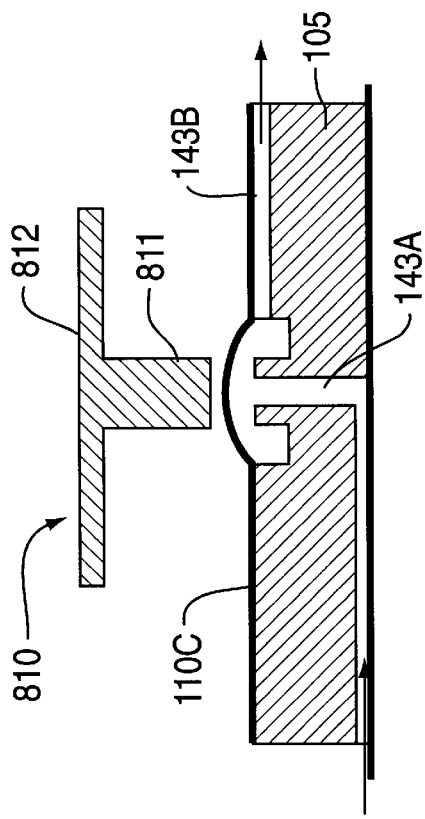
FIG. 5A and 5B show a plunger-type valve mechanism for regulating fluid flow through a cassette.
Figure 5B:
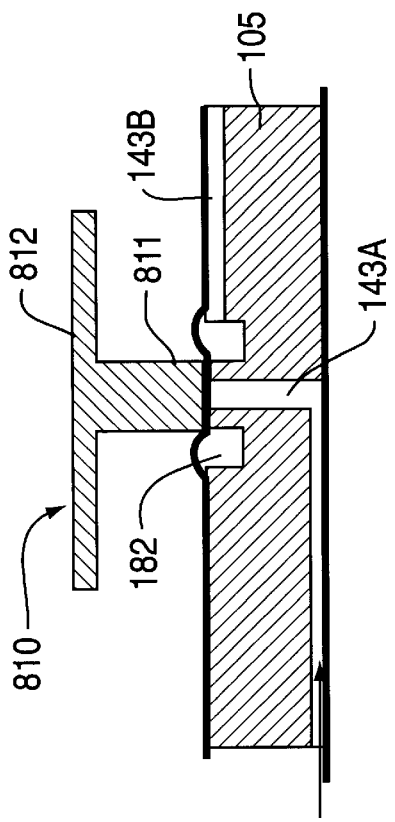
Figure 6:
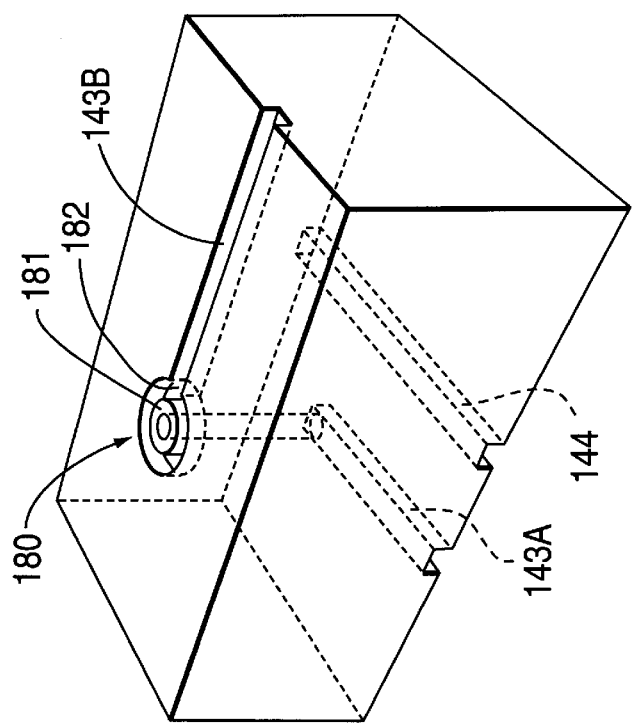
FIG. 6 shows in perspective view the part of a plunger-type valve located in the body of a cassette.

FIGS. 5A, 5B, 6 and 7 illustrate yet another embodiment of the invention that utilizes plunger-type valves to control the flow of fluids in the cassette 100 or cassette 200. The operation of such a plunger-type valve in a cassette 100 or 200 is illustrated above with reference to FIGS. 5A and 5B. Plunger 810 has a plunger rod 811 and a piston 812. In the position illustrated in FIG. 5A, plunger rod 811 is withdrawn away from such that third film 110C, which is embossed to protrude away from the seat 181 of valve 180, does not interfere with fluid flow from alpha third fluid exchange channel 143A, into valve 180, and out through beta third fluid exchange channel 143B. In FIG. 5B, plunger rod 811 presses film 110C against valve seat 181, blocking fluid flow. FIG. 6 shows a three-dimensional view of valve 180, including valve seat 181 and valve trough 182.

The plunger 810 can be constructed of numerous durable materials including without limitation a plastic such as polycarbonate or metal such as stainless steel or aluminum or the like. The diameter of plunger rod 811 is typically from about 20 to about 100 µm, preferably about 60 µm, while piston 812 typically has a diameter from about 100 to about 300 µm, preferably about 200 µm. Preferably, the ratio of the cross-sectional area of the piston 812 to that of the plunger rod 811 is at least about 10-fold, thereby providing a corresponding mechanical advantage.

Figure 7:
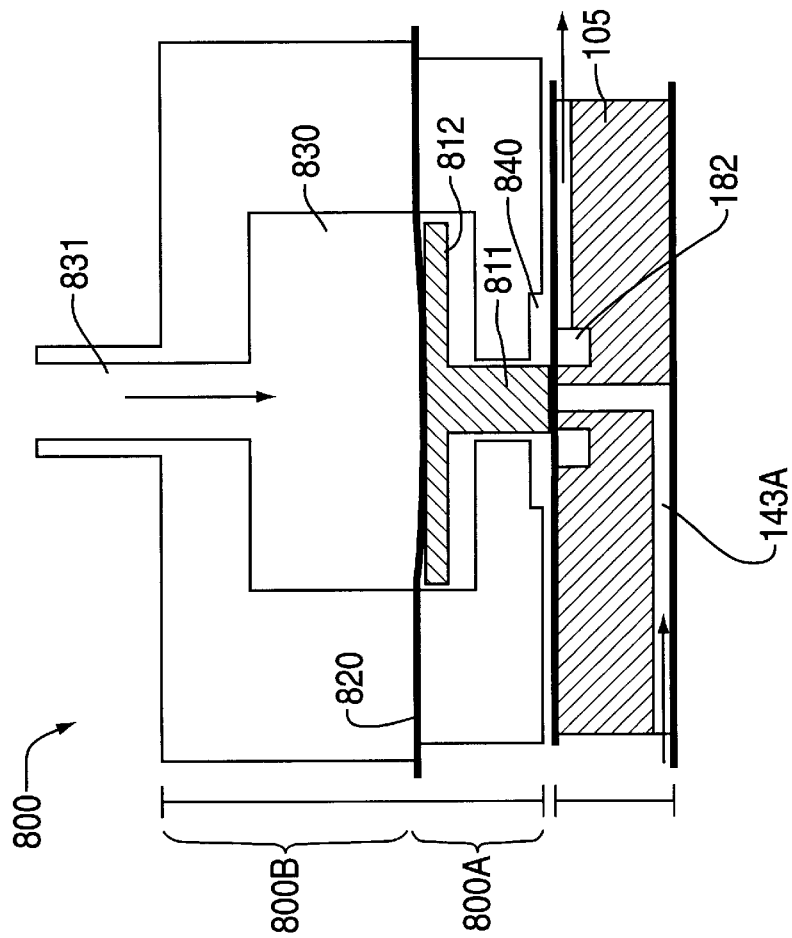
FIG. 7 shows the parts of a plunger-type valve located outside the cassette (i.e., in the instrument).

A pneumatic mechanism for operating plunger 810 is illustrated in FIG. 7. Instrument 900 (not shown) has a pneumatic device 800 formed of first portion 800A and second portion 800B which can be joined together, for instance, by bolts, rivets, adhesives or snap-fitting pieces. Interposed between the first and second portions 800A and 800B is flexible gasket 820, which can be formed of a suitable film such as poly (2-chloro-1,3-butadiene) (e.g., Neoprene, DuPont de Neumours, Wilmington, Del.) or silicon rubber. Flexible gasket 820 can be held in place by the clamping action of first and second portions 800A and 800B, which adherent force can be supplemented using heat sealing or adhesive. Pneumatic cavity 830 is formed in both first and second portions 800A and 800B and has a cavity inlet 831. Fluid, preferably a gas, is inserted through cavity inlet 831 to pressurize the part of pneumatic cavity 830 located above the gasket 820 and cause the gasket 820 to press against plunger 810, causing plunger 810 to press against valve seat 181. In the absence of such fluid pressure in pneumatic cavity 830, pump induced pressure in third fluid exchange channel 143A is sufficient to displace (a) third upper cover into displacement cavity 840 and (b) plunger 810 from the valve seat 181, thereby allowing flow. Pneumatic device 800 can be formed of numerous durable materials including without limitation a plastic such as polycarbonate or metal such as brass or aluminum or the like.

As an alternate to the above method of plunger actuation, other methods may be used which do not employ the piston. These include motor driven cam or screw, and external hydraulic or pneumatic cylinders.

Figure 8A:
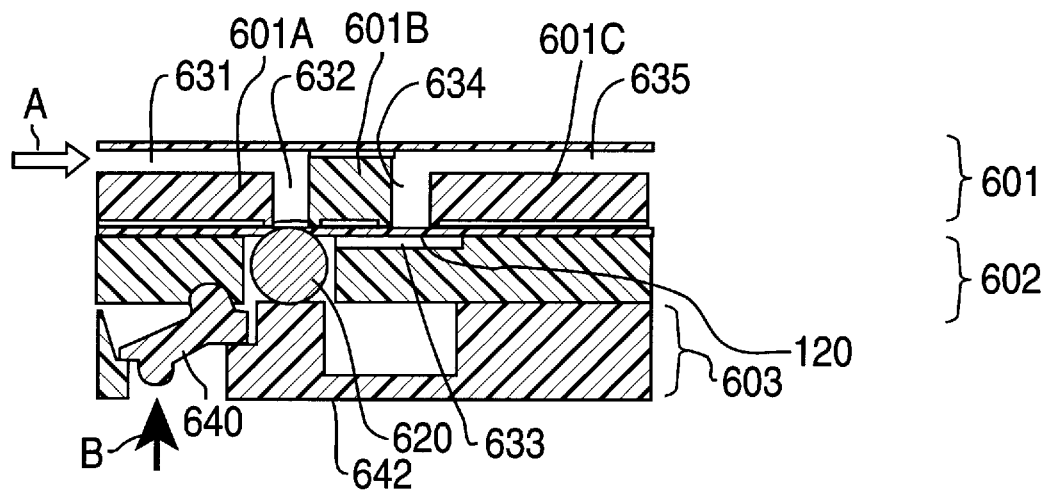
FIGS. 8A, 8B and 8C show various configurations of valve mechanisms for regulating fluid flow through a cassette.
Figure 8B:
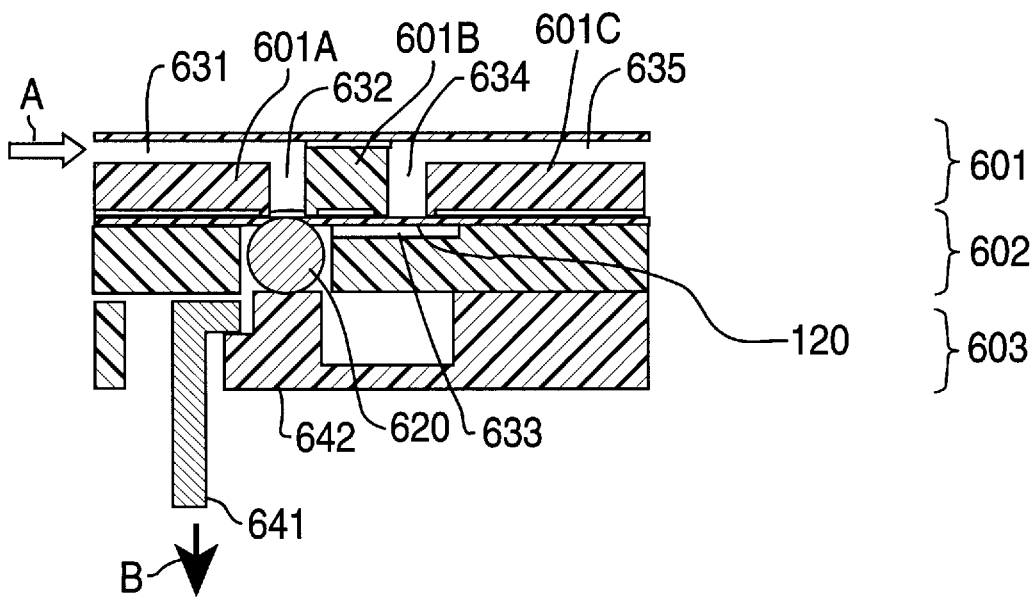
Figure 8C:
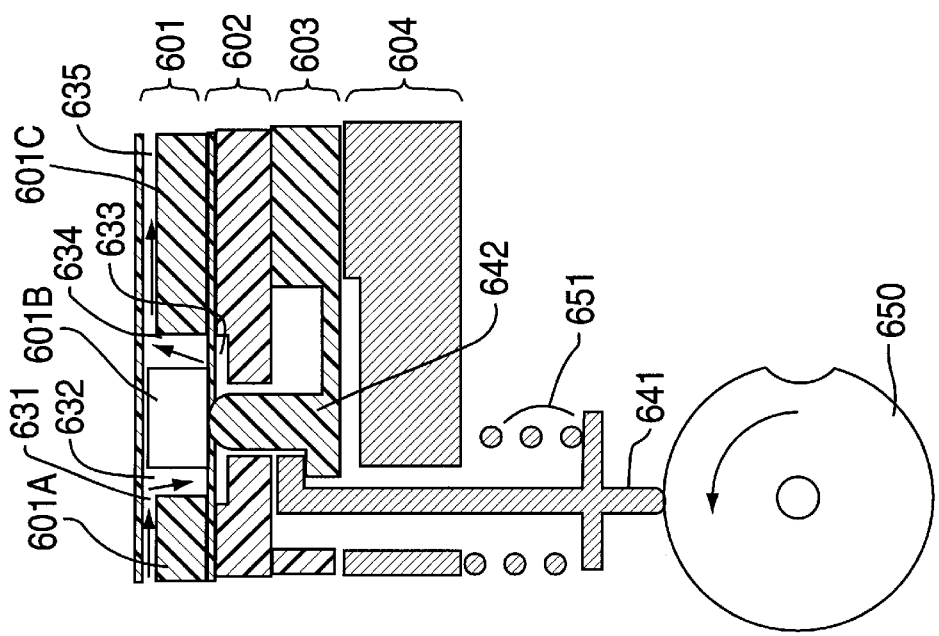

In another valve embodiment of the invention shown in FIG. 8A with reference to another cassette 600 (not shown). Valve ball 620 is used to press lower film 120 flush against the lower surface of first body layer 601 so as to block fluid flow through hole 632. Valve ball 620 can be fabricated of any suitably material such as nylon, high density polyethylene, polycarbonate and the like. Lower film 120 is sealed to portions 601A and 601C of first body layer 601, but typically is not sealed to portion 601B. The sealing between lower film 120 and portions 601A and 601C can be done using, for instance, adhesives or by clamping the membrane between body layer 601 and second body layer 602. First body layer 601, second body layer 602 and third body layer 603 can be joined together using, for instance, by bolts, rivets, adhesives or snap-fitting pieces. Pressure can be applied to valve ball 620 to press it against or release it from lower film 120 in a number of ways. Note that the valve is designed so that valve ball 620 will automatically center itself to properly seat itself against first layer 601. FIG. 8A shows a spring loaded lever 640 that allows a push motion to open the valve, where force is applied as indicated by arrow "B". A push rod 643 (not illustrated) can be used to so engage spring loaded lever 640. FIG. 8B illustrates another embodiment that uses pull rod 641 to open the valve. The function of both spring loaded level 640 and pull rod 641 depend on the spring 642 formed from third body layer 603. Both types of rods can be activated by a cam 650 that is driven by a shaft 652 (not illustrated). In operation, liquid flow is, for instance, in the direction indicated by arrow "A" and proceeds by first conduit 631 and second conduit 632. When valve ball 620 is seated against first body layer 601, the valve is closed and flow is stopped. As the valve ball 620 is withdrawn, lower film 120 deforms in response to fluid pressure, into cavity 633 to form third conduit 633A (not shown) linking second conduit 632 with fourth conduit 634. Fourth conduit 634 connects with fifth conduit 635. FIG. 8C illustrates the use of a cam 650 to activate a pull rod 641 that is spring loaded with pull rod spring 651. All of the various pull rods 641 and pull rod springs 651 can be contained in a single base plate 604, such as that shown in FIG. 8C, which can be attached to the instrument 900. The valve of FIG. 8C also differs in employing a pinch foot 621 instead of a valve ball 620 and in seating the pinch foot 621 against portion 601B instead of against the opening of second conduit 632. In the illustrated embodiments of FIGS. 8A—8C, the valves are normally in the closed position. The positioning of the valves can be programmed and activated by controller 960 (not shown). To further ensure that fluid flow is blocked prior to attaching the cassette 600 to the base plate, temporary membranes or seals can be employed to maintain the various fluids in their chambers. These membranes could be broken by applying a light pressure. Alternatively, the fluids could be frozen prior during storage to attaching the parallel reaction device to the base plate.

Alternatively, second and third body layer 602 and 603, respectively, can be designed to be separable from first body layer 601, which contains fluid exchange channels and fluid chambers. In this embodiment, prior to joining these separable parts, the valve locations are not strongly closed to fluid flow, although the lower film 120 can rest securely enough against portion 601B to prevent inadvertent fluid flow. Where the valve includes a valve ball 620, a ball retention film 615 is usefully sealed to the upper side of second body layer 602 to assure that the value ball 620 does not fall out of the device. The advantage of separating these pieces is that the portions of the parallel reaction device containing mechanical elements can be re-used while the fluid-handling portion can be disposed of.

Figure 9A:
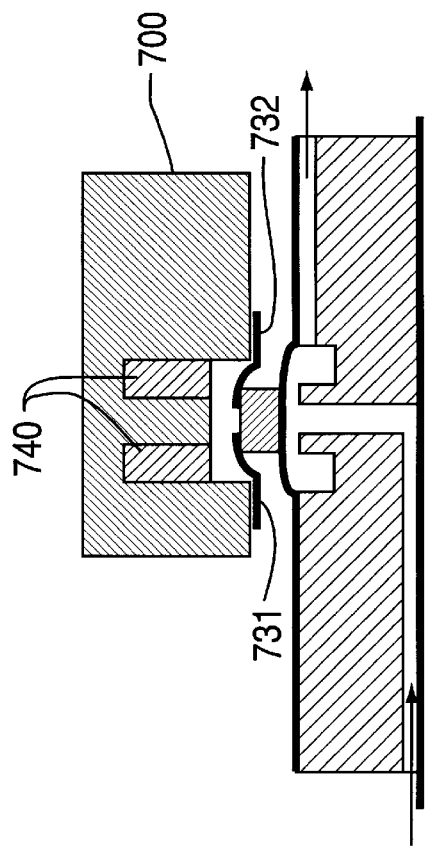
FIGS. 9A and 9B show a magnetic spring valve mechanism for regulating fluid flow through a cassette.
Figure 9B:
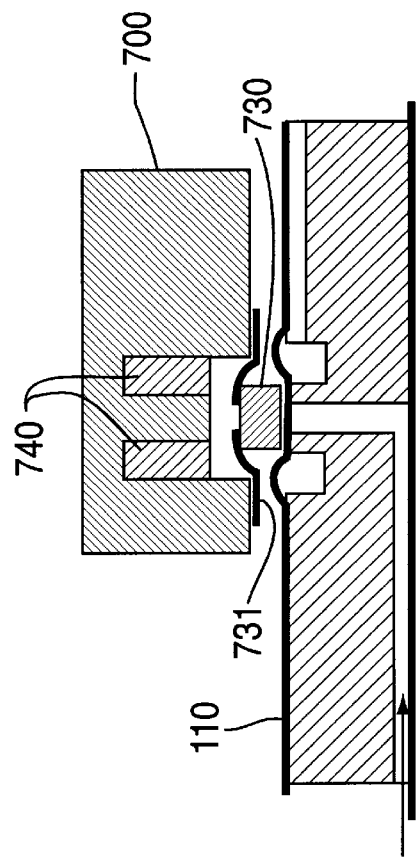

FIG. 9B shows a closed electromagnetic valve 380 for use in controlling the flow of fluids in a cassette 300. Located in a portion 700 of instrument 900, the electromagnetic valve 380 has a spacer 730 that is pressed against a flexible upper film 110 by first spacer spring 731 and second spacer spring 732. The first and second spacer springs 731 and 732 or the spacer 730 are sufficiently magnetic or magnetically permeable that they can be drawn away from upper film 110 by activating electromagnetic coils 740. In FIG. 9A, The electromagnetic valve 380 is shown in the open position with spacer 730 electromagnetically drawn away from valve seat 381.

Auxiliary Blocks

Figure 10:
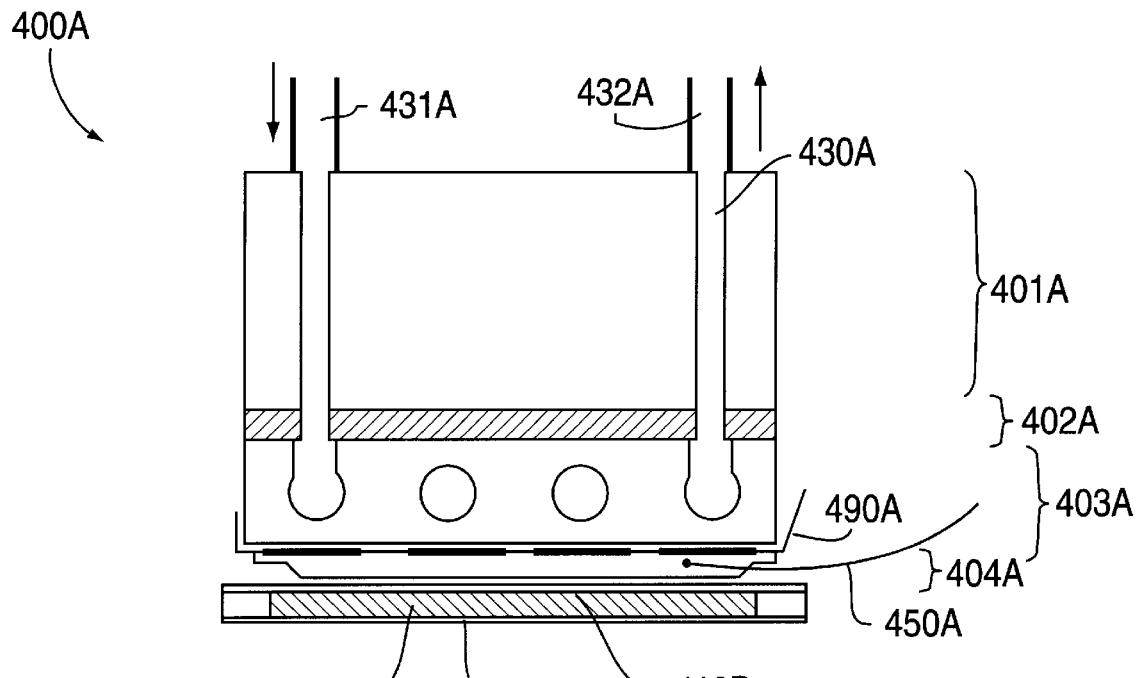
FIG. 10 shows a support device for rapidly heating and cooling a reaction chamber and providing a foot-pad for a foot-pad pump.

FIG. 10 illustrates a part of instrument 900, reaction cell servicing device 400, having upper auxiliary block 400A for moving fluids into or out of a reaction chamber 160. Preferably, there will be a corresponding, upwardly oriented lower auxiliary block 400B located underneath reaction chamber 160. Upper auxiliary block 400A is honeycombed with upper conduit 430A. Upper conduit 430A has an upper inlet 431A and an upper outlet 432A. First upper portion 401A of upper auxiliary block 400A is fabricated of any suitably sturdy material, but is preferably constructed of the same material as third upper portion 403A. Second upper portion 402A is preferably fabricated of a heat-insulating material, such as, without limitation, nylon, polycarbonate and the like. Third and fourth upper portions 403A and 404A are preferably fabricated of a heat-conductive material, such as, without limitation, aluminum, copper, sintered beryllia, and the like. Upper portions 401A–404A can be joined using, for instance, bolts, rivets, adhesives or snap-fitting pieces. Upper electrical heaters 440A are positioned adjacent to the reaction chamber 160.

The upper and lower heaters 440A and 440B are generally thin layers of conductive material that is separated from the heat-conductive upper and lower sections 402A and 402B of upper and lower auxiliary blocks 400A and 400B by a thin electrical insulation layer. Such an insulation layer is formed, for example, by direct deposition onto the substrate. For example, silicon nitride can be deposited from the gas phase or aluminum oxide can be deposited using a liquid carrier. The conducting layer forming upper and lower heaters 440A and 440B are, for example, deposited by vacuum evaporation (e.g., for a nichrome conducting layer) or by deposition from the vapor (e.g., for an indium tin oxide conducting layer). Alternately, pre-formed heater sheets are cemented to the substrate, for instance using an epoxy cement or the adhesive recommended by the vendors. Appropriate heaters can be obtained from Elmwood Sensors Inc. (Pawtucket, R.I.) or from Omega Engineering Inc. (Stamford, Conn.). Typically, individual heater elements have planar dimensions appropriate, alone or in combination with electrically coupled heater elements, to match the size of the reaction chamber to be heated.

Figure 11A:
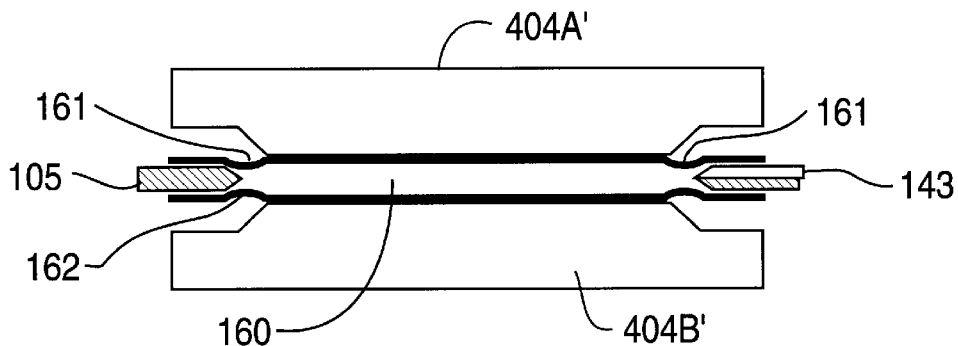
FIGS. 11A and 11B show the operation of a foot-pad pump on a reaction chamber.
Figure 11B:
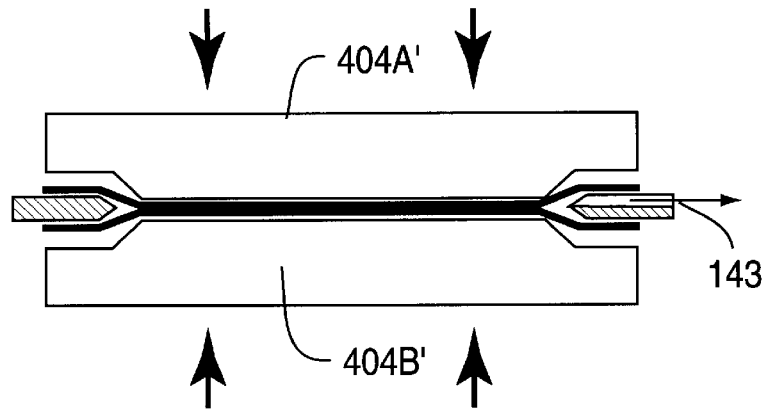

Fourth upper portion 404A constitutes an upper foot-pad 404A' for a foot-pad pump that operates to pump fluid out of a reaction chamber 160. In this context, where a foot-pad is associated with a heating and cooling device, it is preferably fabricated of a material with high thermal conductivity such as aluminum, copper, sintered beryllia, and the like. The operation of the foot-pad pump 460, which includes lower foot-pad 404B', is illustrated in FIGS. 11A and 11B. When the upper and lower foot-pads 404A' and 404B' are withdrawn away from reaction chamber 160, the reaction chamber 160 can be filled with fluid (see FIG. 11A). When the upper and lower foot-pads 404A' and 404B' are brought towards each other (see FIG. 11B), fluid in reaction chamber 150 is pushed out either through second fluid exchange channel 142 or third fluid exchange channel 143. The embossing at location 161 (for the upper film 110B) or at location 162 (for lower film 120), allows the two films to be pushed together without substantial stretching. The embossing of upper film 110B and lower film 120 is done, for instance, by applying suitably shaped, heated dies.

Preferably, instrument 900 has a device for pumping and controlling reaction cell temperature, such as reaction cell servicing device 400, for each reaction chamber 160 in the cassette 100 or 200.

Figure 12:
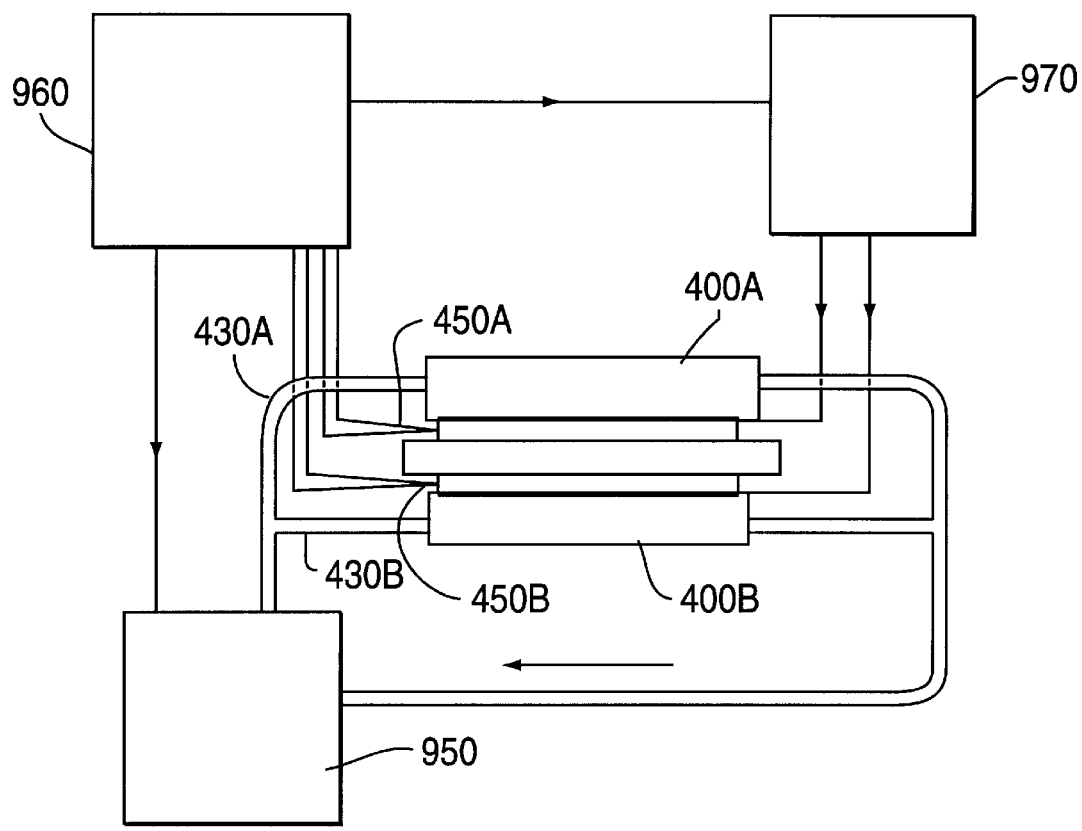
FIG. 12 shows a schematic of accessory support devices for rapidly heating or cooling a reaction chamber.

FIG. 12 shows a schematic of the accessory support devices for the upper auxiliary block 400A of FIG. 11. Water is propelled through upper and lower conduits 430A and 430B, respectively, from pump and water cooler console 950. Pump and water cooler console 950 further includes fluid valves operating under the control of controller 960. Electrical current is supplied to upper and lower heaters 440A and 440B, respectively, by power supply 970, which is controlled by controller 960. Controller 960 receives input from upper and lower thermal sensors 450A and 450B, respectively.

Figure 13:
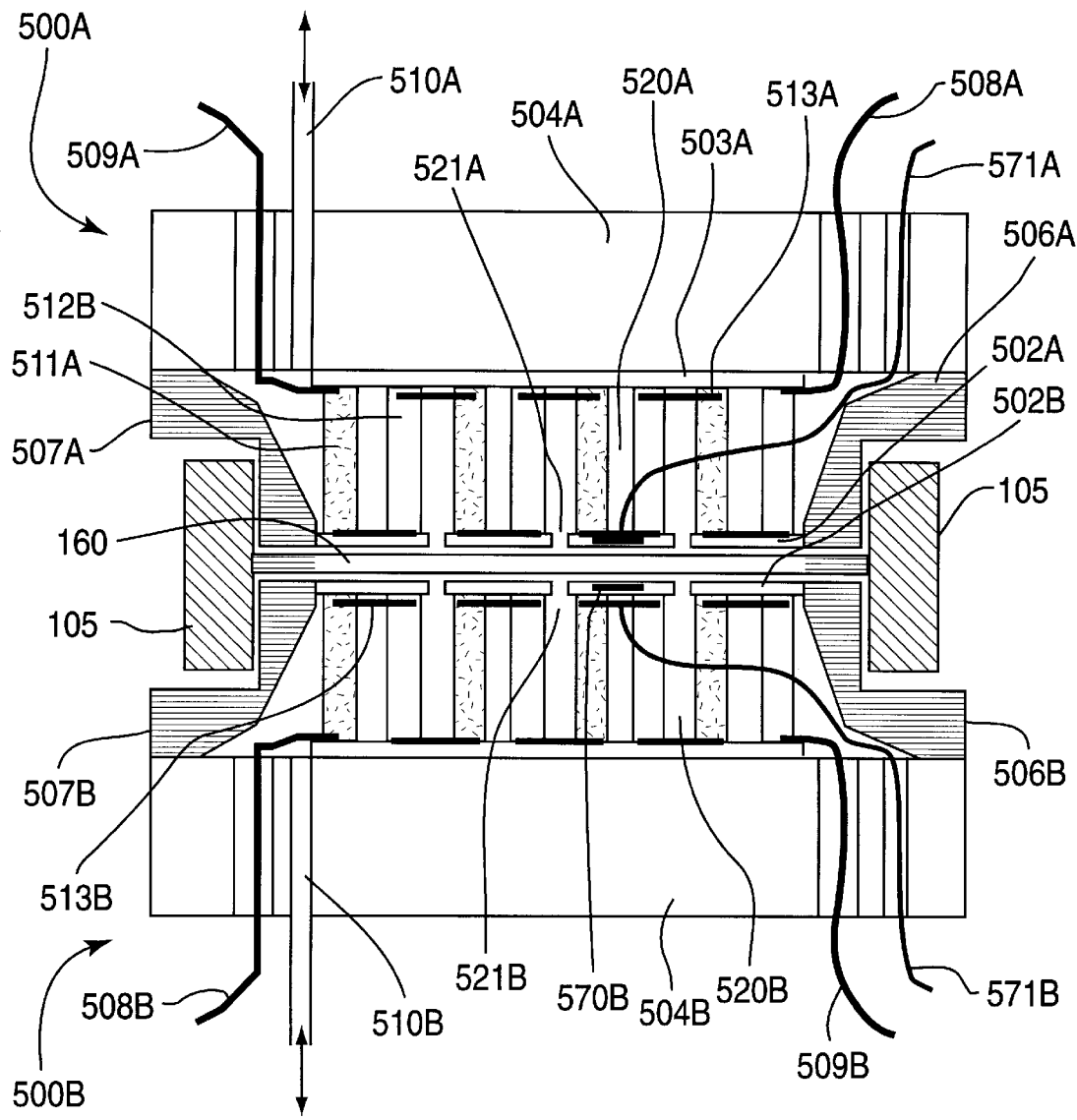
FIG. 13 shows another mechanism for rapidly heating or cooling a reaction chamber.

In FIG. 13, upper auxiliary block 500A includes a set of paired first and second upper thermoelectric blocks 511A and 512A, respectively, while lower auxiliary block 500B has a set of paired first and second lower thermoelectric blocks 511B and 512B, respectively. First upper and first lower thermoelectric blocks 511A and 511B, respectively, are made of p-type semiconductor material, while second upper and second lower thermoelectric blocks 512A and 512B, respectively, are made of n-type semiconductor material. The thermoelectric blocks 511 and 512 are electrically connected in series by upper and lower connectors 513A and 513B as illustrated to form thermoelectric heat pumps. Such thermoelectric heat pumps are available for instance from Tellurex Corp., Traverse City, Mich. and Marlow Industries, Dallas, Tex. Upper and lower gas inlet/outlets 510A and 510B are connected to upper and lower manifolds 520A and 520B, respectively, formed by the space between the upper and lower thermoelectric blocks 501A and 501B. Upper and lower manifolds 520A and 520B (which are made up of the space between thermoelectric blocks) are connected, respectively, to an upper plurality of passageways 521A or a lower plurality of passageways 521B. The outer portions of upper and lower auxiliary blocks 500A and 500B are upper and lower heat sinks 504A and 504B, respectively, which are preferably constructed of a heat-conductive material such as, without limitation, aluminum, copper, sintered beryllia, and the like. First upper air-tight collar 506A, second upper air-tight collar 507A, first lower air-tight collar 506B and second lower air-tight collar 507B help form upper and lower manifolds 520A and 520B. Upper and lower thermal sensors 570A and 570B are connectable to a controller or a monitoring device by upper and lower leads 571A and 571B, respectively.

It will be recognized that upper end-plate 502A viewed from underneath or lower end-plate 502B viewed from above would have a series of holes which are the outlets of upper and lower passageways 521A and 521B. Another attribute of the auxiliary blocks 500A and 500B is that the thermoelectric blocks typically are arrayed in three dimensions rather than two.

Heating is achieved by applying voltage of the proper polarity to upper first and second leads 508A and 509A and to lower first and second leads 508B and 509B. Cooling is achieved by reversing the polarity of the voltage. An important variable in the operation of these heating and cooling devices is temperature uniformity. To increase temperature uniformity, upper and lower first end-plates 502A and 502B are preferably constructed of a material of high thermal conductivity, such as sintered beryllia. Other suitable materials include, without limitation, ceramics containing metallic aluminum. Preferably, the thermoconductivity of end-plates 502A and 502B is at least about 0.2 watt·cm$^{-1}$·K$^{-1}$, more preferably at least about 2 watt·cm$^{-1}$·K$^{-1}$. The upper and lower temperature sensors 570A and 570B can be, without limitation, thermocouples or resistive sensors. The upper and lower sensors 570A and 570B can, for example, be deposited on upper and lower first end-plates 502A and 502B as thin films or they can be in the form of thin wires embedded into holes in upper and lower first end-plates 502A and 502B.

Upper and lower auxiliary blocks 500A and 500B provide an alternate method of applying pressure to second upper film 110B and lower film 120 to push fluid out of reaction chamber 160. When gas pressure is applied through upper gas inlet/outlet 510A and corresponding lower gas inlet/outlet 510B (not shown) of lower auxiliary block 500B, the gas exiting upper and lower pressurized fluid channels 521A and 521B (not shown) forces upper and lower films 110 and 120 together, thereby forcing fluid from reaction chamber 160.

Upper or lower auxiliary block 500A or 500B can contain a plurality of upper or lower pressurized fluid channels 421A or 421B, respectively, which are used to operate a gas pressure flow control means. The fluid within these channels typically is a gas such as oxygen or nitrogen. Gas of higher than atmospheric pressure can be applied to the upper or lower pressurized fluid channels 421A or 421B from, for instance, a pressurized gas canister or a pump applied to upper or lower gas inlet/outlet 410A or 410B. A vacuum, usually a partial vacuum, can be applied to the upper or lower pressurized fluid channels 421A or 421B using, for instance, a vacuum pump. Numerous mechanisms for controlling the pressure of the pressurized fluid channels will be recognized by those of ordinary skill in the engineering arts.

Figure 14:
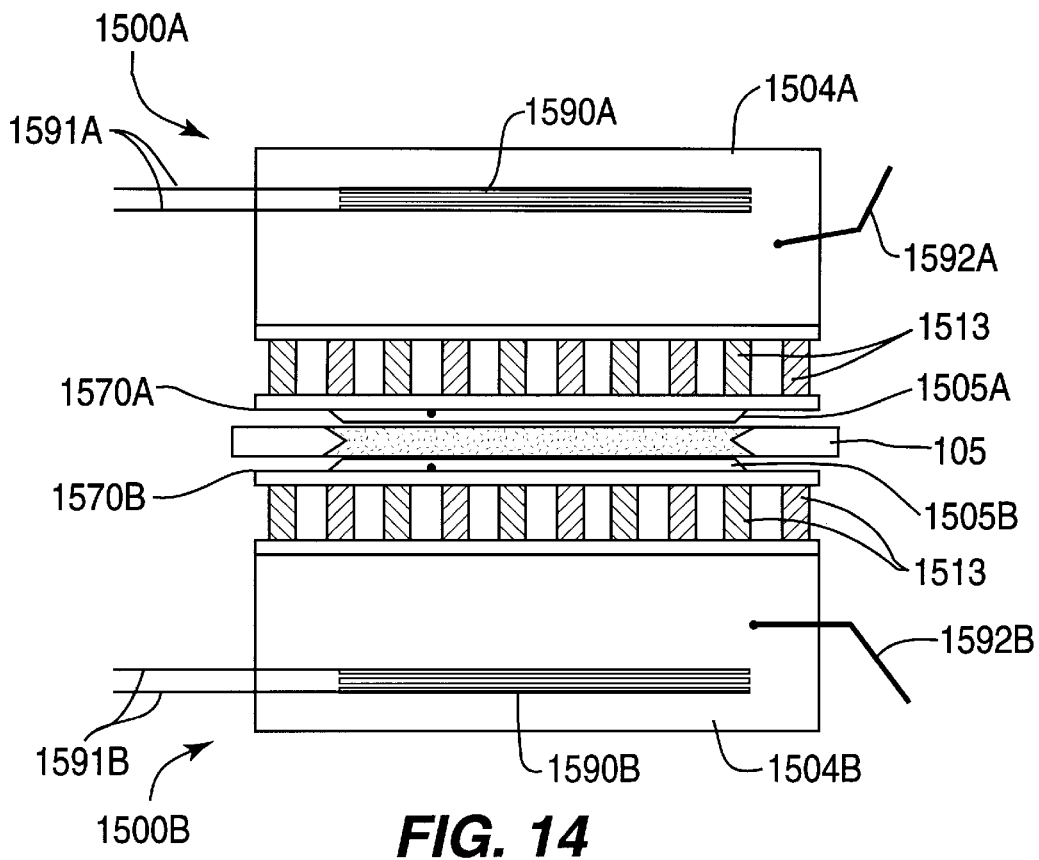
FIG. 14 shows yet another mechanism for rapidly heating or cooling a reaction chamber.

FIG. 14 illustrate another upper auxiliary block 1500A and lower auxiliary block 1500B that use thermoelectric heat pumps but use a foot-pad pump instead of a gas-pressure mediated pumping device. Upper and lower foot-pads 1505A and 1505B are used to pump fluid out of reaction chamber 160. Thermoelectric blocks 1513 are used to heat or cool as described above. Upper and lower heat sink thermal sensors 1592A and 1592B are located in upper heat sink 1504A and lower heat sink 1504B, respectively. Upper heat sink heater 1590A and lower heat sink heater 1590B (connected to electrical power via upper leads 1591A and lower leads 1591B, respectively) are used to transfer heat to the thermoelectric blocks 1513, thereby allowing thermoelectric blocks 1513 to operate at a higher temperature range. Upper and lower sensors 1570A and 1570B are used to monitor the temperature of the adjacent reaction chamber 160.

The speed with which the temperature of the reaction chamber 160 is increased or decreased is important for optimizing some nucleic acid amplification assays. During the temperature cycling important for some nucleic acid amplification assays, it is important to operate at a relatively lower temperature where the nucleic acid sample is enzymatically reproduced and at a higher temperature where the nucleic acid sample is melted to separate the two strands of the nucleic acid. During the period when the assay apparatus cycles between the two preselected temperatures believed to be appropriate for a given nucleic acid amplification, various unwanted chemistries can be expected to occur. For instance, as the temperature increases from the lower temperature, the replication enzyme can be expected to continue to function, although not necessarily with the appropriate accuracy of replication achieved at the prescribed lower temperature. At the higher temperature set point, this unwanted enzymic activity is inhibited by the high temperature. Thus, it is important to rapidly change the reaction temperature between the two operating temperature plateaus.

One mechanism by which the temperature can rapidly be changed in the reaction chamber is illustrated in FIG. 10. Assume that the reaction chamber 160 is operating at lower plateau temperature "G". Under these conditions, cooling water does not flow through upper conduit 430A or corresponding lower conduit 430B (not shown). The temperature is maintained by intermittently operating upper and lower heaters 440A and 440B when the temperature in reaction chamber 160 lowers beneath a temperature of G minus X (where X is a temperature differential). At a preprogrammed time, the temperature is raised to higher plateau temperature "H" by activating upper and lower heaters 440A and 440B until a temperature is reached that will lead to a temperature stabilization at temperature H. Water flow through upper and lower conduits 430A and 430B can be activated to minimize temperature overshoots if needed. Temperature H is maintained by intermittently operating upper and lower heaters 440A and 440B when the temperature of the reaction chamber 160 lowers beneath a temperature of H minus Y (where Y is a temperature differential). To cycle back to temperature G, the controller activates the pump 451 (not illustrated) of console 450 to cause cooling water to flow through upper and lower conduits 430A and 430B.

The performance of such a heater device and cooling device can be simulated using a heat transfer simulation computer program using a finite element approximation of the heat flow equation. The simulation is conducted with the following assumptions: the thickness of the reaction chamber 160 is 0.5 mm, the upper and lower films were 0.1 mm thick and the insulation between the heater and the auxiliary block was 0.025 mm thick. Such a simulation has determined that a jump from 25° C. to 75° C. can be achieved within 3.2 seconds, where, after 3.2 seconds, the temperature in the reaction chamber is substantially uniform. The reciprocal cooling step can be achieved within about 3 seconds, resulting in a substantially uniform temperature in the reaction chamber. Preferably, after this cooling step the variation in temperature in the reaction chamber is no more than about 0.1° C.

Using the heating and cooling devices of the present invention, including the device described in the immediately preceding paragraph, reaction chamber 160 temperatures between about −20° C. and about 100° C. can be maintained.

In one preferred embodiment, when the parallel reaction device includes more than one reaction flow-way, each such reaction flow-way will include at least one reaction chamber 160 which will have at least one heating and cooling device made up of thermoelectric blocks 501 (such as the heating and cooling device described in the paragraph immediately above) capable of being aligned with a side of the reaction chamber. More preferably, each such reaction chamber 160 will have a heating and cooling device on each of two opposing sides. In another preferred embodiment, the cross-sectional area of upper or lower first end-plate 502A or 502B substantially matches the largest cross-sectional area of the reaction chamber 160 to which it is intended to transfer heat.

The principles of temperature cycling for a reaction chamber 160 heated and cooled with upper and lower auxiliary blocks 500A and 500B or upper and lower blocks 1500A and 1500B are the same as those outlined above for the upper and lower auxiliary blocks 400A and 400B of FIG. 10.

In another embodiment, the reaction chamber 160 is heated and cooled by passing a heated or cooled fluid, preferably a gas, either directly over one or more surfaces of the reaction chamber 160 or through a heat exchange apparatus that can be positioned adjacent to one or more surfaces of the reaction chamber 160. The apparatus illustrated in FIG. 10 can be modified to operate pursuant to this embodiment by (a) removing (or not using) the upper and lower heaters 440A and 440B and (b) adding a heater for heating the fluid. The parallel reaction device preferably has two fluid management systems, one for a hotter fluid and another for a cooler fluid, together with the valving required to inject the hotter or cooler fluid into the tubing leading to the reaction chamber 160 as appropriate for maintaining a given temperature in the reaction chamber. Particularly where the heating and cooling fluid is a gas, the temperature of the gas soon after it has passed by the reaction chamber 160 will provide a useful indication of the temperature of the reaction chamber 160.

Where the auxiliary blocks act as foot-pads or for other footpads, mechanical or electromechanical methods of drawing the foot-pads towards or away from the fluid chamber on which it acts are well known and include solenoids, pneumatically activated plungers, screw mechanisms and the like.

Auxiliary blocks and other features useful in conjunction with this invention are described in U.S. patent application Ser. No. <11772A>, filed Oct. 31, 1996, titled "Assay System," Docket No. DSRC 11772A, which is incorporated herein in its entirety by reference.

Miscellaneous Pumps

Pumping action can also be achieved using, for instance, peristaltic pumps, mechanisms whereby a roller pushes down on the flexible film of a fluid chamber to reduce the volume of the chamber, plungers that press on the flexible film of a fluid chamber to reduce its volume, and other pumping schemes known to the art. Such mechanisms include micro-electromechanical devices such as reported by Shoji et al., "Fabrication of a Pump for Integrated Chemical Analyzing Systems," *Electronics and Communications in Japan,* Part 2, 70: 52–59, 1989 or Esashi et al., "Normally closed microvalve and pump fabricated on a Silicon Wafer," *Sensors and Actuators,* 20: 163–169, 1989 or piezo-electric pumps such as described in Moroney et al., "Ultrasonically Induced Microtransport," *Proc. MEMS,* 91: 277–282, 1991.

Detection Devices

In a preferred embodiment, at least one reaction chamber 160 has a transparent retaining wall that is generally formed of upper film 110 or lower film 120 (or two retaining walls are transparent). Reaction chamber 160 can be a chamber where a reaction occurs, such as one of lysing reaction chambers 340 or reaction chambers 380 (see FIG. 3), it can be a supply chamber containing samples, controls or reagents, such as supply chambers 350, 360 and 390, or it can be a storage chamber, such as one of storage chambers 399A–E. The parallel reaction device in this embodiment preferably includes a light source capable of directing light to the transparent upper or lower film 110 or 120 and a detection device for detecting (a) the light reflected from an illuminated reaction chamber 160, (b) the light transmitted through an illuminated chamber 160, or (c) the light emissions emanating from an excited molecule in a chamber 160. A membrane is "transparent" if it is 80% transparent at a wavelength useful for detecting biological molecules.

The detection device can incorporate optical fibers, optical lenses, optical filters or other optical elements. Alternatively, where detection uses fluorescence, detection and quantitation can be done by photographing the detection channel 295 under appropriate excitation light. With fiber optics or other suitable optical devices, the size of the detection system that is adjacent to the parallel reaction device is minimized. This size minimization facilitates incorporating the detection system together with a temperature control device (described more fully below) into the parallel reaction device. A particularly preferred light source is a solid state laser. The size of these light sources also facilitates incorporating a number of auxiliary components about the parallel reaction device. When a nucleic acid amplification is conducted in an parallel reaction device that incorporates current technology solid state lasers, the method used to detect amplified nucleic acid uses a dye that absorbs light at a wavelength higher than about 600 nm to indicate the presence of amplified nucleic acid, as described below. Examples of such dyes include Cy5™, one of a series of proprietary cyanine class dyes. Cy5™, and the related dyes, are products of Biological Systems, Inc. (Pittsburgh, Pa.). This particular dye is relatively small, absorbs at about 650 nm and emits a fluorescent signal at about 667 nm. Other, larger suitable dyes include structures derived from seaweed such as allophycocyanin and allophycocyanin-conjugated reagents (Sigma Chemical Co., St. Louis, Mo.). These dyes absorb in the 630–750 nm range. The relatively long wavelengths of the excitation light described above avoid much of the background fluorescence associated with biological materials, plastics or other possible components of the cassette 100. A preferred solid state laser source is a Laser Max, Inc. (Rochester, N.Y.) Model LAS 200-635.5, which emits a light with a wavelength at a maximum of 4. Other calorimetric detection methods, for instance those utilizing biotin-avidin binding to associate horse radish peroxidase with a hybridized pair of polynucleotide sequences, can be used.

Signals from the detection device typically will be input into a controller 960, where they can be used to determine the presence, or absence, of material assayed for and the magnitude of the signal indicating the presence of the material. From these data, the amount of assay material can be calculated and the quality of the assay as indicated by the controls can be quantitated. This information is then stored for the assay report listing.

Figure 15A:
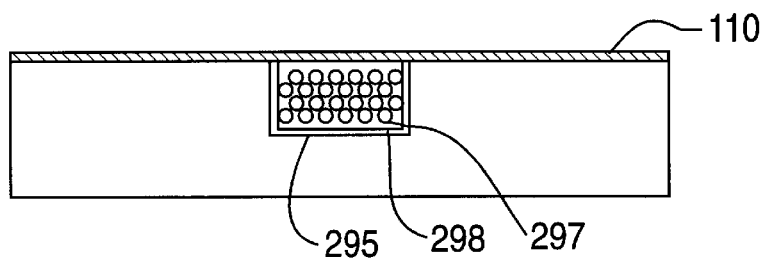
FIGS. 15A and 15B show two side views of a detection channel.
Figure 15B:
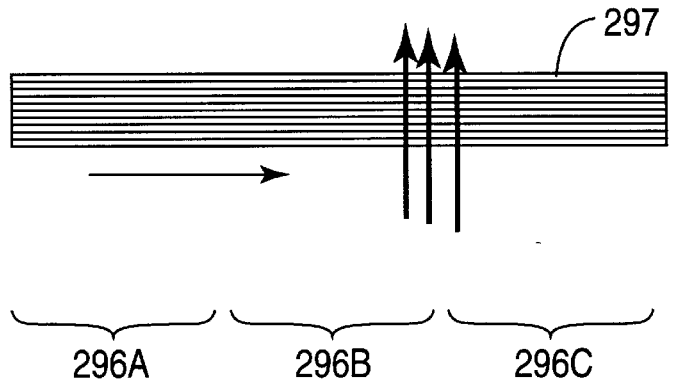

In a preferred embodiment, the cassette has one or more detection channels 295. One such detection channel 295 is illustrated in FIGS. 15A and 15B. It is made up of a number of fibers 297, which together preferably transmit at least about 50% of light of a wavelength useful in the detection procedure, confined to the detection channel 295. The fibers 297 can be bound in place for instance by cementing or crimping. The fibers 297 can be fabricated of glass or suitably transparent plastics. The fibers 297 are preferably between about 5 $\mu$m and about 50 $\mu$m in diameter, more preferably about 20 $\mu$m. The detection channel typically has a width and depth of no more than about 3,000 $\mu$m, preferably between about 200 $\mu$m and about 1,000 $\mu$m. Microchannels between the fibers 297 allow liquid to flow through the detection channel 295. A detection-mediating molecule is bound to the fibers 297. Preferably the detection-mediating molecule is an oligonucleotide that hybridizes with the nucleic acid to be amplified in a nucleic acid amplification reaction and the nucleic acid amplification reaction utilizes primers having a detectable moiety. The detection-mediating molecules are bound to the fibers 297 by known methods. Preferably, discrete bands on the fibers such as first band 296A, second band 296B and third band 296C have separate detection-mediating molecules, which could be, for instance, designed to detect two separate species to be amplified in a nucleic acid amplification reaction and to provide a control for non-specific hybridizations. To manufacture the banding pattern of bound molecules, oligonucleotide synthesis procedures that utilize photo-cleavable protecting groups and masks to protect certain bands 296 from photocleavage can be used. Such synthesis procedures are described in U.S. Pat. No. 5,424, 186 (Fodor et al.). The instrument 900 is preferably designed to provide heat control at the detection channels 295 for conducting hybridization reactions. In a preferred embodiment, the sides 298 of the detection channel 295 are coated with a reflective coating so that light incident from above will reflect and twice pass through the detection channel 295. Such a reflective coating is provided by metalizing, for instance using a sputtering or evaporation process.

Alternatively, the detection channels 295 contain membranes 299 (not shown), such as a nylon membrane, to which a hybridization probe has been bound. If two or more hybridization probes are used, they are each bound to a specific region of the membranes 299 using "dot blot" procedures such as are described in Bugawan et al., "A Method for Typing Polymorphism at the HLA-A Locus Using PCR Amplification and Immobilized Oligonucleotide Probes" *Tissue Antigens* 44: 137–147, 1994 and Kawasaki et al., "Genetic Analysis Using Polymerase Chain Reaction-Amplified DNA and Immobilized Oligonucleotide Probes: Reverse Dot-Blot Typing", *Methods in Enzymology* 218: 369–381, 1993. As described above, the amplification product hybridized with the bound probe or probes has attached—via the amplification primers—a detectable moiety.

Note that for cavities in the cassette 200 intended for use in detection, such as detection channels 295, in a preferred embodiment of the invention the upper film 110 over the cavity is replaced with a cover 110' selected for its optical properties, such as, without limitation, a cover 110' made of optical quartz. Because pumping is effected elsewhere in the cassette, the cover 110' does not have to be flexible like an upper film 110.

While in a preferred embodiment detection is done in situ in the cassette, in other embodiments the products of chemical reactions effected in the cassette are removed and detection methods or chemistries are done elsewhere, including in a different cassette.

Paramagnetic Beads and High Field Gradient Magnet

Paramagnetic beads useful for facilitating chemical processes conducted in a cassette 100 are available from several sources including Bang Laboratories (Carmel, Ind.) for beads lacking conjugated biomolecules, Dynal (Lake Success, N.Y.) for beads conjugated to various antibodies (for instance, antibodies that bind to the CD2 cell-surface receptor) and CPG (Lincoln Park, N.J.) for beads with a glass matrix and a variety of surface bonded organics. For applications where it is anticipated that the beads will be washed into and out of reaction chambers, each bead will preferably have a diameter of less than about 1 mil, more preferably, less than about 0.5 mil, which diameter facilitates entry and exit through the channels by which material is inserted or evacuated from the reaction chamber 160. For applications where the beads are anticipated to remain in the reaction chamber 160, in one embodiment of the invention, the diameter is preferably sufficiently large to preclude their entry into these channels. The entrances to such channels within a reaction chamber 160 are preferably positioned or designed so as to minimize the chance that a channel will be blocked by a bead that settles over the channel's entryway.

Figure 16:
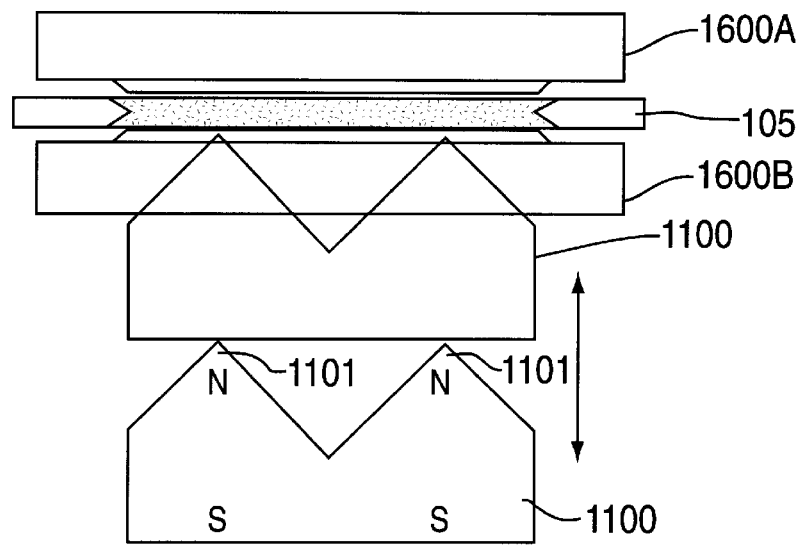
FIG. 16 shows an example of a magnet useful for locking paramagnetic beads at a certain location in a cassette.

In a preferred embodiment, the beads are locked in place using magnetic fields. To generate sufficient movement among the beads, it has been determined that the magnet used should preferably generate a sufficient magnetic field gradient within a reaction chamber 160. Such magnets can be constructed by forming sharp edges on highly magnetic permanent magnets, such as those formed of rare earths, such as the neodymium-iron-boron class of permanent magnets. Such a permanent magnet is available from, for example, Edmund Scientific (Barrington, N.J.). Sharp edges of dimensions suitable for a particular reaction chamber 160 are, for example, formed by abrasive grinding of the magnetic material. An example of such a shaped magnet 1100 is shown in FIG. 16, where the magnet has a roof-shape at one of the poles. The illustration shows a preferred embodiment where there are two roof shapes and illustrates that the magnet can be brought adjacent to or can be removed from a cassette such as cassette 100 or cassette 200. In the illustration, lower auxiliary block 1600B has slots (not visible) that allow the magnet 1100 to be placed adjacent to cassette 100 or 200. This magnet suitably has dimensions such that the length of the peak of the roof-shape matches the cross-sectional size of a reaction chamber 160. To maximize the field gradient acting on the paramagnetic beads, the peak 1101 of the magnet 1100 is placed adjacent to the reaction chamber or other structure in which the beads are located. The paramagnetic beads are held in place by leaving the peak 1101 adjacent to the beads. By moving the magnet with its peak 1101 adjacent to the beads, the beads are impelled to move with the magnet. Another way in which high magnetic field gradients can be achieved is to make uniform slices of a magnetic material and use an adhesive to join the slices in alternating N to S orientations. Such alternating slice magnets have high magnetic field gradients at the junctions of the slices.

The sharp-edged magnets described above are effective in adhering the paramagnetic beads in one place and in moving beads located, for instance, in a fluid exchange channel or in a reaction chamber, from one location to another. Such magnets thus can help retain the paramagnetic beads in one place, for instance when a fluid in a reaction chamber 160 is being removed from that chamber but it is desirable to leave the beads in the chamber. Magnets with locations having high magnetic field gradients that are particularly suitable for use in this context are described in U.S. Provisional patent application Ser. No. 60/006,202, filed Nov. 3, 1995, titled "Magnet," Docket No. DSRC 11904P, which is incorporated herein in its entirety by reference.

Various cell binding beads (e.g., beads having bound antibodies specific for a certain subset of cells) can be used to adhere selected cells from a population of cells. The beads can be locked in place, for instance magnetically if the beads are paramagnetic, while non-adherent cells and fluids are washed away. Thus, cell-binding beads can be used to concentrate small sub-populations of cells.

In synthetic chemistry applications, the beads suitably have attachment sites for coupling the building blocks of chemicals or polymers.

Septum Manufacture

Figure 17A:
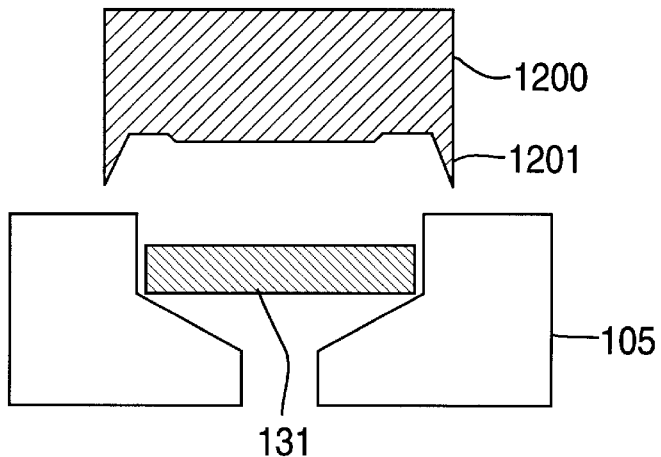
FIGS. 17A and B show a device for mounting a septum to the cassette.
Figure 17B:
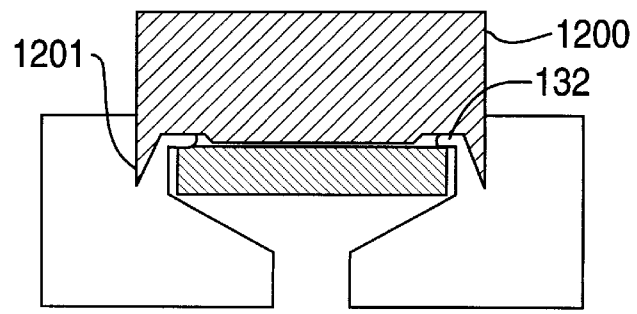

A septum 131 can be fixed in place in inlet 130 using heated die 1200, as illustrated in FIGS. 17A and 17B. The die 1200 is heated sufficiently so that the angled, sharp edges 1201 cut into body 105 and move melted material 132 such that it locks the septum 131 in place.

Controller

The controller 960 typically will be a microprocessor. However, it can also be a simpler device comprised of timers, switches, solenoids and the like. The important feature of controller 460 is that it directs the activation of the means for impelling a fluid, the valves and the heating and cooling device, according to a pre-set or programmable schedule that results in the operation of an assay protocol, such as the protocol outlined below. Preferably, the controller 460 receives input indicating the temperature of the reaction chambers of the parallel reaction device and is capable of adjusting its control signals in response to this input.

PCR Procedures Using the Assay System of the Invention

Often an important variable in PCR reactions is the amount of interfering cellular debris, including membrane fragments and cellular chemicals such as enzymes, fats and non-target nucleic acid, present in the sample to be assayed. Ideally, only highly purified nucleic acid is used as the sample subjected to a PCR amplification. However, such purification is not practical with the small amounts of tissue or fluid available for a diagnostic assay. Further, given the sensitivity of the assay to contamination by environmental sources of nucleic acid, a nucleic acid purification step can increase the likelihood of getting a false positive result. In some areas of diagnostic or forensic PCR this concern about interference by cellular debris has been eased somewhat by improvements in the characterization of PCR reaction conditions, such that often much cruder nucleic acid samples can be used without adverse effect. See Rolfs et al., *PCR: Clinical Diagnostics and Research,* Springer Lab, 1992 (particularly Chapter 4 et seq.). See, also, the literature available with such commercial products as GeneReleaser (BioVentures, Inc., Murphreesboro, Tenn.), Pall Leukosorb™ media (Pall, East Hills, N.Y.) and Dynbeads® DNA Direct™ (Dynal, Lake Success, N.Y.). (On PCR procedures, see generally, Ausubel et al., *Current Protocols in Molecular Biology,* John Wiley & Sons, New York and *PCR: A Practical Approach,* IRL Press, 1991.) Nonetheless, it is desirable to have the capability of at least removing the cellular debris associated with the cell membranes of the cells that may be present in the sample. Such a technique for use in conjunction with the parallel reaction device of the invention is described below. Such a cleanup step can be applied when needed to achieve the needed level of sensitivity or accuracy, or omitted if not needed.

It is preferable to conduct parallel control PCR reactions when conducting PCR. One control omits sample from the reaction or uses a sample previously characterized as negative. Another control introduces a known amount of a purified nucleic acid that is known to contain the sequence or sequences that the PCR reaction is designed to amplify. These types of controls can be accomplished on multiple parallel reaction devices or, more preferably, in separate reaction flow-ways on the same parallel reaction device whereby each reagent is distributed from a single source to all of the reaction flow-ways.

Another control technique used in PCR is to design the PCR reaction so that it will amplify multiple nucleic acid segments, each of which can be indicative of a disease or a genetic circumstance or marker. The different segments can be amplified in multiple reactions or in the same reaction chamber. If amplified in the same chamber, that binding competition between the various primers can necessitate extending the time, in each amplification cycle, spent at the replication temperature.

One method for removing cellular debris from a sample involves binding the cells in the sample to a bead that has attached thereto an antibody specific for a cell surface molecule found on the cells. Beads that bind to the CD2 white blood cells or to *E. coli* bacteria (such as the 0157E strain) are available from Dynal (Lake Success, N.Y.). An ever-growing family of cell-surface molecules found on mammalian cells, bacterial cells, viruses and parasites has been characterized and antibodies against the majority of these molecules have been developed. See, e.g., *Adhesion Molecules,* C. D. Wegner, ed., Academic Press, New York, 1994. Many of these antibodies are available for use in fabricating other types of cell-affinity beads (for instance, from Sigma Chemical Co., St. Louis, Mo.). The cells can be adhered to the antibodies on the beads and lysed to release their nucleic acid content. The lysis fluid together with the released nucleic acid can be moved to a separate compartment for further processing, leaving behind the beads and their adherent cellular debris.

The lysis fluid used to release nucleic acid from the sample cells can also interfere with the PCR reaction. Thus, in some protocols it is important to bind the nucleic acid to a substrate so that the lysis fluid can be washed away. One such support is provided by beads that bind to DNA, such as glass beads that bind to DNA by ionic or other interactions such as Van der Waals interactions and hydrophobic interactions. Suitable beads, with surfaces chemically treated to maximize the number of interaction sites, are available from, for example, BioRad (Hercules, Calif.). Paramagnetic beads with a number of DNA binding surfaces, such as nitrocellulose or nylon-coated surfaces, can be useful in operating the invention. In some embodiments, it is desirable for the beads to be paramagnetic so that they can be manipulated using magnetic forces. Paramagnetic glass beads are manufactured by CPG (Lincoln Park, N.J.). Once the nucleic acid is bound to the beads, the lysis fluid can be washed from the beads. The nucleic acid can be amplified with the beads present.

The lysis fluid used to release nucleic acid from the cells in a sample typically includes a detergent, preferably nonionic, and a buffer, usually the buffer used in the PCR amplification reaction. The pH of the lysis fluid is preferably from about pH 7.8 (for protease K-containing lysis fluids, for example) to about pH 8.0 (for phenol-mediated lysis, for example), typically about pH 8.0. Suitable detergents include, without limitation, Sarkosyl and Nonidet P-40. Other components can includes salts, including $MgCl_2$, chelators and proteases such as proteinase K. Proteinase K can be inactivated by heating, for instance, to about 100° C. for about 10 minutes. Depending on the composition of the lysis buffer, it can be more or less important to wash the lysis buffer away from the nucleic acid prior to conducting the amplification assay.

The amplification buffer used to support the amplification reaction will typically include the four deoxynucleotide triphosphates (NTPs) (e.g., at a concentration of from about 0.2 mM each), a buffer (e.g., Tris.HCl, about 10 mM), potassium chloride (e.g., about 50 mM) and magnesium chloride (e.g., about 1 to 10 mM, usually optimized for a given PCR assay scheme). The pH is preferably from about pH 8.0 to about pH 9.0, typically about pH 8.3. Other components such as gelatin (e.g., about 0.01% w/v) can be added. The individual primers are typically present in the reaction at a concentration of about 0.5 $\mu$M. The amount of sample nucleic acid needed varies with the type of nucleic acid and the number of target nucleic acid segments in the nucleic acid sample. For genomic DNA, where each cell in the sample has about 2 copies of target nucleic acid, a concentration of about 10 $\mu$g/ml is desirable.

For simplicity, the polymerase used in the procedure is a heat-resistant DNA polymerase such as Taq polymerase, recombinate Taq polymerase, Tfl DNA polymerase (Promega Corp., Madison, Wis.), or Tli DNA polymerase (Promega Corp., Madison, Wis.). Heat stability allows the PCR reaction to proceed from cycle to cycle without the need for adding additional polymerase during the course of the reaction process to replace polymerase that is irreversibly denatured when the reaction vessel is brought to a DNA strand separation temperature. Preferably, the DNA polymerase used has the increased accuracy associated with the presence of a proofreading, 3' to 5' exonuclease activity, such as the proofreading activity of the Tli DNA polymerase.

Blood provides one of the more convenient samples for diagnostic or genetic PCR testing. For most genetic testing, from about 10 to about 50 $\mu$l of blood is sufficient to provide enough sample DNA to allow for PCR amplification of specific target segments. For fetal cell analysis, however, as much as about 20 mls, which may contain as few as about 400 fetal cells, can be required. Such large sample volumes require concentration, for instance, using the methods described above. For testing for microbial diseases, the concentration of target nucleic acid in the sample can be quite low (e.g., no more than about 2–5 fg per bacterial genome). Thus, when using the parallel reaction device to test for such microbes, concentration methods may again be required.

To specifically amplify RNA, it is necessary to first synthesize cDNA strands from the RNA in the sample using a reverse transcriptase (such as AMV reverse transcriptase available from Promega Corp., Madison, Wis.). Methods for conducting a PCR reaction from an RNA sample are described, for example, in Ausubel et al., *Current Protocols in Molecular Biology*, John Wiley & Sons, New York and *PCR: A Practical Approach*, IRL Press, 1991. To prepare RNA for this purpose, a facile procedure uses a lysis buffer containing detergent (such as 0.5% Nonidet P-40), buffer (e.g., pH 8.3) and suitable salts that has been, immediately prior to use, mixed 1:1000 with a 1:10 diethylpyrocarbonate solution in ethanol. After sample cells have been lysed with this solution, a supernate containing RNA is separated away from a pellet of nuclei by centrifugation. Primer, which is generally the same as one of the primers used in the subsequent PCR cycling reaction, is annealed to the RNA by heating (e.g., to about 65° C.) and subsequently reducing the temperature to, generally, about 37° C. The reverse transcriptase, nucleotide triphosphates and suitable buffer (if not already present) are then added to initiate cDNA synthesis. Generally, a small volume (e.g., about 1.0 to about 2.0 $\mu$l) of material from the cDNA synthesis is added to a solution (e.g., about 50 to about 100 $\mu$l) containing the buffer, DNA polymerase, nucleotide triphosphates and primers needed for the PCR amplification. The temperature cycling program is then initiated.

Hybridization Procedures

The advantages of the parallel reaction device as it relates to conducting PCR reactions also substantially apply to conducting hybridization procedures. The ability of the valves of the parallel reaction device to accommodate elevated temperatures allows the system to be used in hybridization protocols. While hybridization reactions are not as sensitive to contamination as PCR reactions, these reactions are nonetheless very sensitive to contamination, the risk of which is substantially reduced with the disposable system of the invention.

Procedures for conducting hybridizations are well known in the art. See, for example, Ausubel et al., *Current Protocols in Molecular Biology*, John Wiley & Sons, New York and Sambrook et al., *Molecular Cloning: A Laboratory Manual*, 2nd ed., Cold Spring Harbor Press, 1989. In these procedures, a nucleic acid such as (a) a sample source of nucleic acid containing a target sequence, or (b) a probe nucleic acid is bound to a solid support and, after this binding, the remaining binding sites on the support are inactivated. Then, the other species of nucleic acid, which has bound to it a detectable reporter molecule, is added under appropriate hybridization conditions. After washing, the amount of reporter molecule bound to (i.e. hybridized with) the nucleic acid on the solid support is measured.

For instance, a hybridization can be conducted in a reaction chamber in the parallel reaction device, where the reaction chamber contains a nitrocellulose membrane (or another membrane that binds nucleic acid) to which RNA has been bound (for instance, by electrophoretic or capillary blotting from a separation gel, followed by baking). A Northern prehybridization solution can then be introduced into the reaction chamber from one of the fluid chambers.

(The recipes for Northern prehybridization solution (p. A1-40), Northern hybridization solution (p. A1-39), SSC (p. A1-53, 20X recipe) and Denhart's solution (p. A1-14, 100X recipe) of Ausubel et al., *Short Protocols in Molecular Biology*, 2nd Edition, John Wiley & Sons, 1992 are incorporated herein by reference to more fully exemplify the hybridization methods that can be conducted in the parallel reaction device; note that the salmon sperm DNA recited in two of these recipes, which DNA serves as a competitor to reduce nonspecific hybridizations, is typically sheared prior to use.) The membrane and prehybridization solution are incubated overnight at a temperature between about 37° C. and about 42° C., depending on the melting temperature for the interaction between target sequence and the probe sequence. Note that these incubation temperatures are in the range that is generally appropriate given the presence of 50% formamide in the prehybridization and hybridization solutions; for hybridizations conducted without formamide, incubation temperatures are typically higher, such as about 55° C. to about 70° C. The membrane is then exposed to Northern hybridization solution containing melted probe and incubated overnight at the same temperature used in the prehybridization. Following hybridization, the hybridization solution is pushed out of the reaction chamber, the reaction chamber is brought to about 25° C. and a first wash solution (1X SSC, 0.1% w/v sodium dodecyl sulfate) is introduced. After 15 minutes, the wash is repeated. After an additional 15 minute wash, a third and final wash is conducted using 0.25X SSC, 0.1% w/v sodium dodecyl sulfate.

The above outlined hybridization method is exemplary only. Numerous other hybridization methods can be conducted in the assay system, including those described in the following sections of Ausubel et al., *Short Protocols in Molecular Biology*, which are incorporated herein by reference: Unit 2.9, pp. 2–24 to 2–30 and the recipes of Appendix 1 referred to therein; Unit 6.3, pp. 6—6 to 6-7 and the recipes of Appendix 1 referred to therein; and Unit 13.12, p. 13–44 and the recipes of Appendix 1 referred to therein.

Using the parallel reaction device of the invention, the elevated temperatures required for hybridization reactions can be handled in an automated apparatus. For instance, hybridizations can be conducted at a temperature defined by the melting temperature $T_m$. $T_m$ values for any hybridization probe can be calculated using commercially available software such as Oligo TM v4.0 from National Biosciences, Inc., Plymouth, Minn.

Immunological Procedures Using the System of the Invention

In immunoassay procedures, the antibody-antigen binding reactions are generally conducted at room temperature or at a reduced temperature, such as about 4° C. After the binding reactions, positive results are generally indicated by an enzymic reaction, typically mediated by the enzyme alkaline phosphatase, which enzyme reaction is generally conducted at a temperature between about 20° C. and about 40° C. The parallel reaction device of the invention allows these assays to be automated in a system that allows fast and reliable temperature regulation in the temperature range between about 0° C. and about 40° C.

Typically, modern antibody-based screening procedures use a solid support to which an "antigen" (which is a substance that when injected into an animal, often in the presence of "adjuvants" known to enhance antibody production, can cause the animal to manufacture antibodies specific for the antigen) or an antibody has been attached. Alternatively, the antigen is found on the surface of a cell, such as a bacteria or eukaryotic cell, and the cell can function as a solid support.

In one assay (indirect ELISA), the antigen is bound to the support and a sample which may contain a first antibody specific for the antigen and produced by a first animal species is incubated with the bound antigen. After appropriate washing steps, a second antibody from a second animal species, which antibody is specific for antibodies of the first species and is attached to a detectable moiety (such as alkaline phosphatase), is incubated with the support. If the sample contained the first antibody, the second antibody will bind and be detectable using the detectable moiety. For instance, if the detectable moiety is alkaline phosphatase, detection can be conducted by adding a chemical, such as p-nitrophenyl phosphate, that develops a detectable characteristic (such as color or light emission) in the presence of a developing reagent such as a phosphatase enzyme. This assay can, for instance, be used to test blood for the presence of antibodies to the AIDS virus.

In another assay (direct competitive ELISA) that uses a support with bound antigen, a sample which may contain an antigen is incubated with the support together with a limiting amount of an antibody specific for the antigen, which antibody has an attached detectable moiety. Due to competition between the solution phase antigen and the support-bound antigen, the amount of antigen in the sample correlates with reduced amounts of antibody that bind to the support-bound antigen and a weaker signal produced by the detectable moiety.

Another assay (antibody-sandwich ELISA) uses a first antibody specific for an antigen, which antibody is bound to the support. A sample which may contain the antigen is then incubated with the support. Following this, a second antibody that binds to a second part of the antigen, and which has an attached detectable moiety, is incubated with the support. If the sample contained the antigen, the antigen will bind the support and then bind to the detectable second antibody. This is the basis for the home pregnancy test, where the antigen is the pregnancy-associated hormone chorionic gonadotropin.

In another assay (double antibody-sandwich ELISA) that uses a support with bound antibody, a sample which may contain a first antibody from a first species is incubated with a support that has bound to it a second antibody from a second species that is specific for antibodies of the first species. The antigen for the first antibody is then incubated with the support. Finally, a third antibody specific for a portion of the antigen not bound by the first antibody is incubated with the support. The third antibody has an attached detectable moiety. If the sample contained the first antibody, the detectable third antibody will bind to the support.

These and other immunoassays are described in Units 11.1 and 11.2 of Ausubel et al., *Short Protocols in Molecular Biology* (pp. 11–1 to 11–17), which text and the recipes of Appendix 1 cited therein, are incorporated herein by reference.

The following examples further illustrate the present invention but, of course, should not be construed as in any way limiting its scope.

EXAMPLE 1

Cassette Fabrication

The following example illustrates fabrication methods used in constructing cassettes for a microfluidics device of the present invention.

Various cassettes have been fabricated containing components that are shown in FIG. 1. Cassette bodies have been made from high-density polyethylene, both by machining and by molding. The methods of fabrication and demonstrated performance include the following:

Membrane embossing

The membrane covering the cassette body and forming the reaction chambers was embossed prior to sealing to the body. The membrane was stretched on a frame and embossed between positive and negative hot dies. For membranes of polyester/polyethylene laminate, the dies were heated to a temperature of above 140° C. Since this is above the melting point of the polyethylene, the die in contact with the polyethylene was made of polytetrafluoroethylene, to prevent adhesion. A preferable material for embossing is a fluoropolymer/polyethylene laminate which can be given a more permanent deformation at a lower temperature and which has a lower water permeability.

Heat sealing

The membrane was sealed to the cassette body using a hot aluminum die with raised lands corresponding to the heat seal areas. A pressure, corresponding to approximately 150 to 300 psi over the actual seal area, was applied for 1 to 2 seconds. Following application of the pressure, the die was either rapidly quenched by water channels running through the die block, or the die was lifted. Superior results were obtained by quenching the die. With a 2 mil thick membrane of a polyester/low-density polyethylene laminate, sealed to a body of high-density polyethylene, a die temperature of 156° C. was used. A blister 0.5" in diameter sealed in this manner withstood internal pressures in excess of 50 psi.

To preserve uniformity of seal over a cassette of extended size, the cassette regions at the seal were formed into a raised ridge, about 0.01" high. Variation in the amount the die deforms the base material, originating from small variations in cassette thickness, can then occur with a minimum variation in the volume of base material displaced. This ridge structure was found to reduce the extruded material in regions such as the well surrounding a valve.

Bursapak™ structure

The outer seal of the Bursapak™ was made as described above. The center seal was made using a die heated to temperature of about 156° C. This die contained small independently sprung steel pins which contacted the center seal. The lower conductivity of the steel and the air gap between the pins and the die were designed to restrict the amount of heat available for sealing. When the seal was formed at the center in this way, melting of the cassette base material was minimal, although the low-density polyethylene of the membrane was above its melting point. This seal was demonstrated to withstand an internal excess pressure of about 16 psi. Above this pressure, it ruptured as required by the design and released the contents of the Bursapak™ through the central port.

Liquid fill

Liquid fill of both Bursapaks and storage vessels similar to the "waste vessel" of FIG. 1 was achieved. The input needle was connected to a 2-way valve which could be switched between a vacuum pump and a syringe supplying the fill liquid. Following exhaustion of the vessel by the pump, for a few seconds the valve was switched and the vessel filled by the syringe. The filled vessel then contained no air bubbles. Both a septum, as shown in FIG. 1, and a simple entry port were used for filling. Sealing of the entry channel was achieved by a hot rod, as indicated in FIG. 2, which melted the channel closed but kept the polyester component of the membrane sufficiently intact.

Valve operation

Valves, constructed as in FIGS. 1, 5 and 6, were fabricated according to the above descriptions. A molded polyethylene body and polyester/polyethylene membrane was used. Functioning was tested using pneumatically operated steel plungers. With a plunger force of approximately 0.8 lb. and a water pressure of 20 psi, the leakage rate was less than 0.1 microliter per minute.

EXAMPLE 2

PCR Amplification Reaction

The following example illustrates one embodiment of the present invention whereby a PCR amplification reaction is conducted in the context of a cassette in a microfluidics device.

A PCR assay is conducted using the cassette 200 illustrated in FIGS. 4A–4E, the device having alpha through delta first reaction chambers 262A–D, which are used for lysing the cells in the samples, and alpha through delta second reaction chambers 262A–D, with each first reaction chamber 261- second reaction chamber 262 pair forming a separate reaction flow-way 265. The parallel reaction device has a set of one upper auxiliary block, e.g. 1500A and one lower auxiliary block, e.g. 1500B (not shown), for each of first reaction chamber 261 and each second reaction chamber 262. The cassette 200 has pumps for moving fluid from one chamber to another chamber. For instance, the gas pressure flow control means or the foot-pad pumps described above can be used to empty chambers and push the fluid therefrom into another chamber. Valves located between the various chambers contained in the device regulate this flow of fluids between and among the chambers. The reaction protocol is as follows:

1. Each of the four first reaction chambers 261 receives from a connected first supply chamber 251 a suspension in 160 µl of paramagnetic DNA-binding beads having a diameter of 2–4 mils, that can be used in the cell lysis stage to bind the DNA released from the lysed cells (these beads are, e.g., Dynabeads® DNA Direct™, available from Dynal, Lake Success, N.Y.). The beads are locked in place in the lysing reaction chambers 261 using the magnet 1100 and suspending liquid is drained into first waste chamber 271. Alpha first reaction chamber 261A receives a fluid (40 µl) from alpha fifth supply chamber 255A containing purified DNA that includes the amplification sequence being tested for in an amount sufficient to generate a positive result, thereby creating a positive control. Beta first reaction chamber 261B receives from beta fifth supply chamber 255B buffer solution or a biological sample known to not contain the target sequence (40 µl) in place of the sample or positive control, and therefore serves as a negative control. Blood sample (40 µl), stored in sixth supply chamber 256, is drawn into each of gamma and delta first supply chambers 261C and 261D. The first reaction chambers 261 are then filled with a lysis solution (100 µl) that is drawn from alpha, gamma, epsilon and eta third supply chambers 253A, C, E and F, respectively. The lysis solution is a solution of amplification buffer supplemented with 1.0% v/w Tween 20 (Sigma Chemical Co., St. Louis, Mo.). (The lysis solution can be substituted with the solution provided by Dynal.) The temperature of first reaction chambers 261 is now maintained at 56° C.
2. After 10 minutes, the lysis solution is emptied into first waste chamber 271. The lysis solution which exits from alpha and beta first reaction chambers 261A and 261B, respectively, contains the cellular and serum residue of the blood sample. The DNA-binding beads, to which the cellular DNA is bound, remain in first reaction chambers 261.
3. Wash solution (100 µl) composed of amplification buffer (40 mM NaCl, 20 mM Tris-HCl, pH 8.3, 5 mM MgSO$_4$, 0.01% w/v gelatin, 0.1% v/v Triton X-100, Sigma Chemical Co., St. Louis, Mo.) is now introduced into first reaction chambers 261 from the connected second supply chambers 252.
4. After 10 minutes, the wash solution is transferred out of first reaction chambers 261 into first waste chamber 271.
5. Steps 3 and 4 are repeated.
6. Solutions (volume 30 µl) containing appropriate primers for amplifying the target sequence (0.5 µM) are then drawn into first reaction chambers 261 from the connected beta, delta, zeta and theta third supply chambers 253B, 253D, 253F and 253H. Solutions (volume 30 µl) containing the needed nucleotide triphosphates (0.2 mM each), are introduced from the connected alpha, gamma, epsilon and eta fourth supply chambers 254A, 254C, 254E and 254F. Solutions (volume 30 µl) containing Taq polymerase (2 Units, available from Promega Corp., Madison, Wis.) are introduced from the connected beta, delta, zeta and theta fourth supply chambers 254B, 254D, 254F and 254H. The contents of each of first reaction chambers 261 are then transferred to the corresponding one of alpha through delta second reaction chambers 262A–D.
7. The controller then initiates a temperature program modelled on the protocol described by Wu et al., *Proc. Natl. Acad. Sci. USA* 86: 2752–2760, 1989. The program first heats second reaction chambers 262 to a temperature of 55° C. and maintains that temperature for 2 minutes. Next, the controller cycles the temperature between a replication temperature of 72° C. (maintained for 3 minutes) and a DNA strand separation temperature of 94° C. (maintained for 1 minute). After the replication temperature incubation has been conducted 25 times, the material in reaction chambers 262 is analyzed for the presence of the proper amplified sequence.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed:

1. A device for conducting parallel reactions, comprising:
   (a) a cassette formed of a body having an upper surface and a lower surface and including an upper film or a lower film attached to the upper or lower surface, respectively, wherein the upper or lower film is formed of a flexible material;
   (b) two or more reaction flow-ways in the cassette, wherein each reaction flow-way comprises two or more fluid chambers which comprise a first supply chamber and a first reaction chamber having an upper wall and a lower wall, and wherein the fluid chambers are serially connected by first fluid exchange channels;
   (c) a valve for controlling the flow of fluid through a first fluid exchange channel;

(d) a pump for moving fluids into or out of the fluid chambers; and (e) a first inlet port on the cassette connected to a first supply chamber in each reaction flow-way by a second fluid exchange channel.

2. The device of claim 1, wherein the upper and lower walls of each first reaction chamber are formed of a portion of said upper film which is attached to said upper surface, and a portion of said lower film, which is attached to said lower surface and further comprising at least one compression device for bringing the upper and lower walls of the first reaction chambers together to minimize the volume of the first reaction chambers.

3. The device of claim 1, further comprising:

(j) one or more waste chambers; and (k) an exhaust port for evacuating one or more of the first reaction chambers or the waste chambers.

4. The device of claim 1, further comprising:

(o) a permanent magnet that can be positioned adjacent to one or more of the fluid chambers.

5. The device of claim 1, further comprising a valve which comprises a hole extending through the body, further comprising a fluid exchange channel proximate to but not intersecting the hole, and a film having an embossed portion sealed to the body such that the hole and the fluid exchange channel are covered, wherein pressure applied to the film closes the valve.

6. The device of claim 1, further comprising:

(g) one or more second supply chambers, wherein two or more fourth fluid exchange channels connect the second supply chamber to two or more reaction flow-ways, which fourth fluid exchange channels include two or more said valves so that fluid from the second supply chamber can be directed to any one of the connected reaction flow-ways to the exclusion of the other connected reaction flow-ways; and (h) one or more second inlet ports on the cassette each connected to one of the second supply chambers by a separate third fluid exchange channel.

7. The device of claim 6, further comprising:

(i) a fluid chamber interposed between the second supply chamber and the connected reaction flow-way and connected to a fourth fluid exchange channel.

8. The device of claim 1, wherein the body comprises recesses in its upper or lower surface which, together with an associated upper or lower film, form the first and second fluid exchange channels, and a plurality of fluid chambers.

9. The device of claim 8, wherein a fluid chamber is formed in the upper or lower surface and at least one first or second fluid exchange channel is formed on an opposing upper or lower surface located above or below that fluid chamber.

10. The device of claim 8, further comprising:

(f) at least one hole situated in the body so as to connect a first or second fluid exchange channel formed at the upper or lower surface of the body with a first or second fluid exchange channel formed at the other surface.

11. The device of claim 1, further comprising:

(l) a heater for heating one or more of the fluid chambers;

(m) a cooler for cooling one or more of the fluid chambers; and (n) a temperature monitor for monitoring the temperature of one or more of the fluid chambers.

12. The device of claim 11, wherein the heater and the cooler comprise a thermoelectric heat pump attached to a heat sink having a heater element.

13. The device of claim 9, wherein the heater or the cooler can change the temperature of a fluid chamber at a rate of at least about 5° C. per second.

14. The device of claim 1, further comprising (p) a detection chamber or channel having a transparent wall.

15. The device of claim 14, further comprising:

(q) a light source adapted to direct light to the transparent wall of a chamber or channel to illuminate the chamber or channel.

16. The device of claim 15, further comprising:

(r) a light detection device positioned to detect:

(1) the light reflected from an illuminated chamber or channel having a transparent wall, (2) the light transmitted through an illuminated chamber or channel having a transparent wall, or (3) the light emissions emanating from an excited molecule in a chamber or channel having a transparent wall.

17. A device for conducting assays in parallel using fluids that are confined to a disposable cassette comprising:

the disposable assay cassette, which comprises:

(i) at least two reaction flow-ways, including a first reaction flow-way designed to receive and assay an experimental sample and a second reaction flow-way designed to receive and assay a negative control, (ii) for each reaction flow-way, at least one supply chamber connected thereto and containing fluids needed in the assay and at least one reaction chamber, (iii) a negative control supply chamber connected with the second reaction flow-way and containing the negative control, and (iv) a test sample supply chamber connected with the first reaction flow-way designed to receive a test sample through an inlet connected with the test sample supply chamber, valves for controlling the flow of fluids in the cassette, and an instrument comprising a temperature control unit for controlling in parallel the temperature in a reaction chamber in each reaction flow-way, valve actuators for opening and closing the valves in the cassette, and one or more pumps for pushing fluid out of the various supply chambers and reaction chambers of the cassette.

18. The device of claim 17, wherein the cassette further comprises (v) a third reaction flow-way designed to receive and assay a test sample and a positive control, (vi) connecting routes between the test sample supply chamber and both the first and third reaction flow-ways, wherein these connecting routes are controlled by valves that allow selective flow between the test sample supply chamber and either the first or third reaction flow-way, and (vii) a first positive control supply chamber connecting with the third reaction flow-way containing the positive control.

19. The device of claim 17, wherein the cassette further comprises (1) a fourth reaction flow-way designed to receive and assay a positive control, and (2) a second positive control supply chamber connecting with the fourth reaction flow-way containing the positive control.

20. The device of claim 17, wherein the cassette further comprises (v) a third reaction flow-way designed to receive and assay a test sample and a positive control, (vi) connecting routes between the test sample supply chamber and both the first and third reaction flow-ways, wherein these connecting routes are controlled by valves that allow selective flow between the test sample supply chamber and either the first or third reaction flow-way, (vii) a fourth reaction flow-way designed to receive and assay a positive control, (viii) a second positive control supply chamber connecting with the fourth reaction flow-way containing the positive control, and (ix) a first positive control supply chamber connecting with the third reaction flow-way containing the positive control.

21. A method of conducting assays using a device for parallel reactions, which method comprises:

(a) providing the device of claim 17 for conducting assays in parallel, wherein reagents and control materials are pre-loaded into the supply chambers;

(b) inserting a test sample into the test sample supply chamber; and (c) reacting (1) the test sample and (2) the negative control sample in separate parallel flow-ways.

\* \* \* \* \*